US011542503B2

(12) United States Patent
Ryu et al.

(10) Patent No.: US 11,542,503 B2
(45) Date of Patent: *Jan. 3, 2023

(54) USES FOR PREVENTION OR TREATMENT OF BRAIN DISEASES USING MICRORNA

(71) Applicant: BIORCHESTRA Co., Ltd., Daejeon (KR)

(72) Inventors: Jin-Hyeob Ryu, Daejeon (KR); Hyun-Jeong Cho, Daejeon (KR)

(73) Assignee: BIORCHESTRA CO., LTD., Daejeon (KR)

( * ) Notice: Subject to any disclaimer, the term of this patent is extended or adjusted under 35 U.S.C. 154(b) by 43 days.

This patent is subject to a terminal disclaimer.

(21) Appl. No.: 17/039,075

(22) Filed: Sep. 30, 2020

(65) Prior Publication Data

US 2021/0123051 A1    Apr. 29, 2021

Related U.S. Application Data

(63) Continuation of application No. 16/443,700, filed on Jun. 17, 2019, now Pat. No. 10,844,380.

(51) Int. Cl.
*C12N 15/113*    (2010.01)
*A61P 25/28*    (2006.01)

(52) U.S. Cl.
CPC ............ *C12N 15/113* (2013.01); *A61P 25/28* (2018.01); *C12N 2310/113* (2013.01); *C12N 2310/321* (2013.01)

(58) Field of Classification Search
CPC ............ C12N 15/113; C12N 2310/113; C12N 2310/321; A61P 25/28
See application file for complete search history.

(56) References Cited

U.S. PATENT DOCUMENTS

| 5,506,097 | A | 4/1996 | Potter et al. |
| 5,532,219 | A | 7/1996 | McGeer et al. |
| 6,136,861 | A | 10/2000 | Chenard |
| 8,129,515 | B2 | 3/2012 | Esau et al. |
| 8,754,203 | B2 | 6/2014 | Tuschl et al. |
| 10,844,380 | B1 | 11/2020 | Ryu et al. |
| 11,198,908 | B2 | 12/2021 | Ryu et al. |
| 2009/0246136 | A1 | 10/2009 | Williams et al. |
| 2012/0065248 | A1 | 3/2012 | Brown et al. |

FOREIGN PATENT DOCUMENTS

| EP | 2436784 B1 | 9/2013 |
| KR | 20120088009 A | 8/2012 |
| KR | 20150095349 A | 8/2015 |
| WO | WO-2013045652 A1 | 4/2013 |
| WO | WO-2015025995 A1 | 2/2015 |
| WO | WO-2018139759 A1 | 8/2018 |
| WO | WO-2018139819 A1 | 8/2018 |
| WO | WO-2020254990 A1 | 12/2020 |
| WO | WO-2020261227 A1 | 12/2020 |

OTHER PUBLICATIONS

Bartus, R.T., et al., "The Cholinergic Hypothesis of Geriatric Memory Dysfunction," Science, 217(4558):408-417, American Association for the Advancement of Science, United States (Jul. 1982).
Carell, T., et al., A Novel Procedure for the Synthesis of Libraries Containing Small Organic Molecules, Angewandte Chemie International Edition, 33(20):2059-2061, VCH Verlagsgesellschaft, Germany (Nov. 1994).
Carell, T., et al., "A Solution Phase Screening Procedure for the Isolation of Active Compounds From a Library of Molecules," Angewandte CHEMIE International Edition, 33: 2061-2064, VCH Verlagsgesellschaft, Germany (Nov. 1994).
Cho, C.Y., et al., "An unnatural biopolymer," Science 261(5126):1303-1305, American Association for the Advancement of Science, United States (Sep. 1993).
Cohen, J.E., et al., "MicroRNA Regulation of Homeostatic Synaptic Plasticity," Proceedings of the National Academy of Sciences of the United States of America, 108(28):11650-11655, National Academy of Sciences, United States (Jul. 2011).
Coyle, J.T., et al., "Alzheimer's Disease: a Disorder of Cortical Cholinergic Innervation," Science, 219 (4589):1184-1190, American Association for the Advancement of Science, United States (Mar. 1983).
Crooke, S.T., "Antisense Research and Application," Springer-Verlag, Berlin, Germany, 131:103-140, (1998).
Dewitt, S.H., et al., "Diversomers: an approach to nonpeptide, nonoligomeric chemical diversity," Proceedings of the National Academy of Sciences 90(15):6909-6913, National Academy of Sciences, United States (Apr. 1993).
Erb, E., et al., "Recursive deconvolution of combinatorial chemical libraries," Proceedings of the National Academy of Sciences 91(24):11422-11426, National Academy of Sciences, United States (Nov. 1994).
Gallop, M.A., et al., "Applications of combinatorial technologies to drug discovery. 1. Background and peptide combinatorial libraries," Journal of Medicinal Chemistry 37(9):1233-1251, American Chemical Society, United States (Apr. 1994).

(Continued)

*Primary Examiner* — J. E. Angell

(74) *Attorney, Agent, or Firm* — Sterne, Kessler, Goldstein & Fox P.L.L.C.

(57) ABSTRACT

The present disclosure relates to a pharmaceutical composition for preventing or treating a brain disease, more particularly to a pharmaceutical composition for preventing or treating a brain disease, which contains a miR-485-3p inhibitor, and a method for screening an agent for preventing or treating a brain disease, which includes a step of measuring the expression level of miR-485-3p. Because the composition for treating a brain disease, which contains a miR-485-3p inhibitor, can restore the ELAVL2 protein unlike the exiting therapeutic agents for Alzheimer's disease, which are limited only to alleviating symptoms by inducing decreased expression of amyloid beta 42, the present disclosure can fundamentally treat various diseases caused by decreased expression of ELAVL2, such as Alzheimer's disease, autism spectrum disorder, mental retardation, amyotrophic lateral sclerosis, etc. Therefore, the present disclosure is useful for treating brain diseases including Alzheimer's disease fundamentally.

19 Claims, 9 Drawing Sheets

Specification includes a Sequence Listing.

(56) References Cited

OTHER PUBLICATIONS

Hanson, L.R., et al., "Intranasal Administration of CNS Therapeutics to Awake Mice," Journal of Visualized Experiments, (74): e4440, MYJoVE Corporation, United States (Apr. 2013).

International Search Report for Application No. PCT/KR2018/000948, dated May 1, 2018, 2 pages.

Kalra, J and Khan, A., "Reducing Aβ Load And Tau Phosphorylation: Emerging Perspective For Treating Alzheimer's Disease, " European Journal of Pharmacology, 764:571-581, Elsevier Science, Netherlands (Oct. 2015).

Kaminska, B., et al., "Kainate-evoked Modulation of Gene Expression in Rat Brain," Acta Biochimica Polonica, 44(4):781-789, Panstwowe Wydawnictwo Naukowe, Poland (Oct. 1997).

Khachaturian Z.S., "Diagnosis of Alzheimer's Disease," Archives of Neurology, 42(11):1097-1105, American Medical Association, United States (Nov. 1985).

Kiriazis, H and Kranias, E.G. et al., "Genetically Engineered Models with Alterations in Cardiac Membrane Calcium-handling Proteins," Annual Review of Physiology, 62:321-351, Annual Reviews, United States (Feb. 2000).

Krenz. M and Robbins, J., "Impact of Beta-myosin Heavy Chain Expression on Cardiac Function During Stress," Journal of the American College of Cardiology, 44(12), pp. 2390-2397, Elsevier Biomedical, United States (Dec. 2004).

Lee, S.T., et al., "Mir-206 Regulates Brain-Derived Neurotropic Factor in Alzheimer Disease Model," Annals of Neurology, 72(2):269-277, Wiley-Liss, United States (Aug. 2012).

Lou, C., et al., "MiR-485-3p and miR-485-5p Suppress Breast Cancer Cell Metastasis By Inhibiting Pgc-1α Expression," Cell Death & Disease, 7(3):e2159, Nature Publishing Group, England (Mar. 2016).

Lustig, Y., et al., "'RNA Walk' a Novel Approach to Study RNA-RNA Interactions Between a Small RNA and Its Target," Nucleic Acids Research, 38 (1):e5, Oxford University Press, England (Jan. 2010).

Piganeau, N., et al., "A Yeast RNA-hybrid System for the Detection of RNA-RNA Interactions in Vivo," RNA, 12(1):177-184, Cold Spring Harbor Laboratory Press, United States (Jan. 2006).

Scheckel, C., et al., "Regulatory Consequences of Neuronal Elav-Like Protein Binding To Coding and Non-Coding RNAs in Human Brain," Elife, 5: e10421, eLife Sciences Publications, England (Feb. 2016).

Seibenhener, M.L and Wooten, M.W., "Isolation and Culture of Hippocampal Neurons From Prenatal Mice," Journal of Visualized Experiments: JoVE, (65): e3634, MYJoVE Corporation, United States (Jul. 2012).

Zuckermann, R.N., et al., "Discovery of nanomolar ligands for 7-transmembrane G-protein-coupled receptors from a diverse N-(substituted)glycine peptoid library," Journal of Medicinal Chemistry 37(17):2678-2685, ACS Publications, United Kingdom (Aug. 1994).

Burgos, K., et al., "Profiles of Extracellular miRNA in Cerebrospinal Fluid and Serum from Patients with Alzheimer's and Parkinson's Disease Correlate with Disease Status and Features of Pathology," PLoS One 9(5):e94839, Public Library of Science, United States (May 2014).

Cardo, L.F., et al., "MiRNA profile in the substantia nigra of Parkinson's disease and healthy subjects," J Mol Neurosci 54(4):830-836, Springer Link, United States (Oct. 2014).

Chen, L., et al., "Identification of aberrant circulating miRNAs in Parkinson's disease plasma samples," Brain Behav, 8(4):e00941, Wiley Periodicals, United States (Jun. 2018).

Ebrahimkhani, S., et al., "Exosomal microRNA signatures in multiple sclerosis reflect disease status," 7:14293, Nature Publishing Group, United Kingdom Oct. 2017).

Goh, S.Y., et al., "Role of MicroRNAs in Parkinson's Disease," Int J. Mol Sci 20(22):5649, MDPI, Switzerland (Nov. 2019).

Gu, J., et al., "MiR-485-3p modulates neural stem cell differentiation and proliferation via regulating TRIP6 expression," J Cell Mol Med. 24(1):398-404, Wiley, United States (Aug. 2019).

Gui, Y., et al., "Altered microRNA profiles in cerebrospinal fluid exosome in Parkinson disease and Alzheimer disease," Oncotarget 6(35):37043-37053, Impact Journals, United States (Oct. 2015).

Khoo, S.K., et al., "Plasma-based circulating MicroRNA biomarkers for Parkinson's disease," J Parkinsons Dis 2(4):321-331, IOS Press, Netherlands (2012).

Lau, P., et al., "Alteration of the microRNA network during the progression of Alzheimer's disease," EMBO Mol Med 5:1613, John Wiley and Sons, United States (Sep. 2013).

Marti, E., et al., "A myriad of miRNA variants in control and Huntington's disease brain regions detected by massively parallel sequencing," Nucleo Acids Res. 38(20):7219-7235, Oxford University Press, United Kingdom (Jun. 2010).

Martinez, B., et al., "MicroRNAs in Parkinson's disease and emerging therapeutic targets," Neural Regen Res 12(12):1945-1959, Publishing House of Neural Regeneration Research, China (Dec. 2017).

Nair, V.D., et al., "Alterations of miRNAs reveal a dysregulated molecular regulatory network in Parkinson's disease striatum," Neurosci Lett 629:99-104, Elsevier, Netherlands (Jun. 2016).

Rani., A., et al., "miRNA in Circulating Microvesicles as Biomarkers for Age-Related Cognitive Decline," Frontiers in Aging Neuroscience 9: 323, Frontiers Media SA, United States (Oct. 2017).

Ravandis, S., et al., "Circulating Brain-enriched MicroRNAs for detection and discrimination of idiopathic and genetic Parkinson's disease," Movement Disorders: 11 pg., Wiley Online Library, United States (Dec. 2019).

Shigemizu, D., et al., "Risk prediction models for dementia constructed by supervised principal component analysis using miRNA expression data," Communications Biology 2(77): 8 pg, Nature Publishing Group, United Kingdom (Feb. 2019).

Sorensen, S.S., et al., "miRNA expression profiles in cerebrospinal fluid and blood of patients with Alzheimer's disease and other types of dementia—an exploratory study," Transl Neurodegener 5(6):1-12, Cross Mark, United States (Mar. 2016).

Tan, L., et al., "Genome-Wide serum microRNA expression profiling identifies serum biomarkers for Alzheimer's disease," Journal Alzheimer's Disease 40(4):1017-1027, IOS Press, Netherlands (May 2014).

Wang, W.X., et al., "Patterns of microRNA expression in normal and early Alzheimer's disease human temporal: white matter versus gray matter," Acta Neuroopathol 121(2):193-205, Springer+ Business Media, Germany (Feb. 2011).

Weinberg, R.B., et al., "Evidence for a Neuroprotective microRNA pathway in amnestic mild cognitive impairment," Frontiers in Neuroscience 9:430, Frontiers Media SA, United States (Nov. 2015).

Co-Pending U.S. Appl. No. 16/443,705, inventors Ryu,JH., et al., filed Jun. 17, 2019. (Unpublished).

International Search Report and Written Opinion for International Application No. PCT/KR2013/007701, Korean Intellectual Property Office, Republic of Korea, dated Jul. 3, 2014, 20 pages.

Hu, K. et al., "MicroRNA expression profile of the hippocampus in a rat model of temporal lobe epilepsy and miR-34a-targeted neuroprotection against hippocampal neurone cell apoptosis post-status epilepticus," BMC Neuroscience 13:115, BioMed Central, England (Sep. 2012).

Hwang, J. et al., "Epigenetic Mechanisms in Stroke and Epilepsy," Neuropsychology Reviews 38: 167-82, American College of Neuropsychopharmacology, United States (Jan. 2013).

Wei, F. et al., "MicroRNAs in Neural Cell Development and Brain Diseases," Science China Life Sciences 54(12):1103-12, Springer Nature, Switzerland (Dec. 2011).

Dontula, R. et al., "MicroRNA 203 Modulates Glioma Cell Migration Via Robo1/ERK/MMP-9 signaling," Genes & Cancer 4(7-8):285-96, SAGE Publications, England (Jul. 2013).

Watts, J. K., and Corey, D. R., "Silencing disease genes in the laboratory and the clinic," Journal of Pathology 226(2):365-379, John Wiley & Sons, Inc., United States (Jan. 2012).

English machine translation of PCT publication WO2018139819A1, published Aug. 2, 2018, inventor Ryu, J.H., et al., 15 pages (retrieved from Internet on Apr. 12, 2020).

FIG. 4

MicroRNA and Target Gene Description:

| | | | |
|---|---|---|---|
| miRNA Name | [redacted] | miRNA Sequence | GUCAUACACGGCUCUCCUCUCU |
| Target Score | 100 | Seed Location | 841, 1621, 1675 |
| NCBI Gene ID | 1993 | GenBank Accession | NM_001171197 |
| Gene Symbol | ELAVL2 | 3' UTR Length | 2459 |
| Gene Description | ELAV like neuron-specific RNA binding protein 2 | | |

3' UTR Sequence

```
   1 TGAGCTCTTG TCTCAGTCC ATTTATATAT GAAAACTATA CAACAAAGGC AAGTTAAGAG
  61 AAACTTTATA CATTAGTAAA TGTCTTTGTA AGTAGTGTT GAGATGGGGA TAAAATGACT
 121 ACTTAGCATC CTAAGAAATA TGTGAGATTT TTTATTGCTA GTATTTGAAT TAAAACTTCT
 181 TAAATATCTT TTATGTTTGA ATATGGACAA GAGGTACAGG GTTTTTACCT GTCACATTGC
 241 ATTCTATTGC CTTCTTTGAA GAAGGTGGAC CTTTTAAAGT GTTCAGGCTA AGGGAAGACA
 301 TTTCTTTTCT TTTTACATAA CTGCCTTGAA CCTGTGAGTA AATATTGAGG CTTTGTGTTG
 361 TAATTCTTCA GTTGGTTGTG TCTTTTTTTT CCCCCCTTTT TTTGCTTTTT CTGATTAGCT
 421 TTGTGTTGG TTTACATTTA AAGCATTGCT GTTATGTCTG TTTAAGAAAA GTATTTTGAA
 481 GTTTACATTT TTATTTATGA AGTTTAAAAC AGTATTTATT TGTAATTAT GATTGGGTT
 541 GGGGAAGGGG GGGCTACATT ATAAACGCTT ATTGTAAGAA TACTGGAGAA CTTTTCGTAA
 601 AGCAGTAGCT TGCCAAAGAG ATAAGAGCCT CTTTGATGTG GGTTTAAAAA AAGCATCTAT
 661 TTTTATAAAA AAGAAAATTT GGAGAAACTT TTTACTGGTC CTGGAACAAA TATTTTGACT
 721 TGAATACTTT GAGAAATCTC TTCATATGAC ACCTAGTGAG CTTTTAAAAT TTACCAGGAA
 781 ATTTGCACGG GTTGGAAAAT TTAGAAAGAT TTATGGTGTA GAAAATACTT TTGAGATCTT
 841 TGTATGAAAG GAGTAGAATC AATGGGGGA AACACTGCTG GTTCATTTT TGTAATCACC
 901 AGTGGAGCGT CTGATCATCC TGGTTATTAT GTGATAGGTG GCTCACATTG ATTTGTGATT
 961 TTGAAACAAA TAAAAAAAAT TTACAAAAGA ATATATAAGA GCAGGCAAGA AATTTAAATT
1021 ACCGAGAGAT GGGGGAAAAA ATCTGTTCTT CCTAAAGAAA TGCCTTCAGA TAGAGCTCAT
1081 GGTGTTTAGT GATGTACTTG CAGTATTGTT TGAAGAATTG TTTTGTCTTA AGGAAAAAAG
1141 AGTTGGACA TGATTTGTAC TGCAGCCAAAT CAGCAAAAGT GATCTGAGTT GGATATATTT
1201 GAAGGTATTT TGAAAGTTAC GTTCAAGGCT AACACCTGAG CTTTGTGTAA TGTAAATAAG
1261 AGCTTGTGTT TATGAAGCTT TCAGCTAATT TAATTTTTTT TGCCTTACAT GCCAAGTGAT
1321 GTTCAGGTTT TGAATGTTTT TGTATCAGTT TTTTCCTTTG TAAATGGCAT TAACATTGTT
1381 ACTTGAGGTC TTGCTTAATC ACTTTTGTTG TCCTGAGGAC TTGAATTTAC AGTGCATCAG
1441 ATTTGTTGCA AATTTTGTCT GTAGATAGTC TAGCCTTCAGC TGTTTATGGT GATGCTACAT
1501 TTTCGTTTAT AAATATGTTT GTGGTATAAA AAAATGAGTA TAACCATAGG TTTTGAACAA
1561 ATTTCCTTAC ATTTTTCATA CAAAAATCAT AAATATCTGT ATGCTATTGA AATTTAACTT
1621 TGTATGATGC TTAAAAACCA CTATTTGGGG AAATAATAAA ATAAGTCTTT ACCATGTATG
1681 AAAGAAATTT TAAAAAATAC AAAATATTTT CTGATTAGCA TCTAGCTTAT AATAAATTTT
1741 CAAAAAGCT GAAGGCAAAA ATGCCTTCAT CAGGATGCAC TGAGAACTAT ATAGTTACGT
1801 CCTGCTTTTT GTATAAACTG AGATCCTGAC ATGCTTCCCC TTAAACAGG CAATGTCCTA
1861 TGCATAACAT AGTTGTACAT TATCTTTGGG GTTGCTTTGA GTTTATTTT TTATTATTA
1921 AAATTGTAGT TATAAAATTT TTCAGTATAG TACAGTACAT ATACTGTGAG GGGGTGCTA
1981 AAGTGAATAA GCAGTTTTC ATGCTGACCC ACTGAATGCT ATTCAGAAAT CAATTGGCTT
2041 ACCACTTTCT CATATCCTTA GGTGCATTTA GATTGGCAGA GTTAACCTTC TGGGTTTAAA
2101 AAAGAAAAA CACTAAAAAA TAAAATACAT GTATATACTT AAAAAAAAT AATAAGGTTT
2161 CCCTCAAGGG AAAACAGCAG CTACATGCTT CTTTCCTATA CTACTGTAGC AAAGCAAGGC
2221 ATTGATGAGA GGGCATGCAA ATTGTGCTTC ACTTTACAGT GTTTTATCAG AGCACTTAAT
2281 AAAATGTAAG GCTGGTATTT ATTTGAAGTT GTAACGTATG ACTTAATTCA CATCTGTTGG
2341 AATAGAAAAT ATATTCTGTT GAGTATTTAA GAGGCTGTAC ATGTTTCTT TTGTGTTGG
2401 ATTCTTTGTA CTTTTTCATG TTCAGTACAT CAATAAACAA AGTTGAAGGG AAAAAAAAA
```

USES FOR PREVENTION OR TREATMENT OF BRAIN DISEASES USING MICRORNA

CROSS-REFERENCE TO RELATED APPLICATIONS

This application is a continuation application of U.S. application Ser. No. 16/443,700, filed Jun. 17, 2019, which is incorporated by reference in its entirety.

REFERENCE TO SEQUENCE LISTING SUBMITTED ELECTRONICALLY VIA EFS-WEB

The content of the electronically submitted sequence listing in ASCII text file (Name: 4366_0120001_SeqListing_ST25.txt; Size: 2,030 bytes; and Date of Creation: Sep. 23, 2020) filed with the application is herein incorporated by reference in its entirety.

TECHNICAL FIELD

The present disclosure relates to a use of miR-485-3p for preventing or treating a brain disease, more particularly to a pharmaceutical composition for preventing or treating a brain disease, which contains a miR-485-3p inhibitor, and a method for screening an agent for preventing or treating a brain disease, which includes a step of measuring the expression level of miR-485-3p.

BACKGROUND OF THE DISCLOSURE

Alzheimer's disease is the most common form of dementia. 75% of patients with dementia have Alzheimer's disease. In most cases, Alzheimer's disease begins in people over 65 years of age, although it can occur earlier in rare cases. In the United States, about 3% of the population aged 65-74 years, about 19% of the population aged 75-84 years, and 50% of the population aged over 85 years suffer from this disease. In Korea, according to a recently reported study on a rural region, about 21% of the population aged over 60 years in the rural region showed dementia, and 63% of them had Alzheimer's dementia. In 2006, 266,000 people around the world had the disease. It is expected that the disease will occur in one out of every 85 people in 2050.

The treatment of Alzheimer's disease has recently focused on the fact that Alzheimer's disease may be caused by impaired cholinergic signaling and transmission in the cerebral cortex and hippocampus (Bartus et al., *Science.* 217 (4558): 408-14 (1982) and Coyle et al., *Science.* 219(4589): 1184-90 (1983)).

Because these regions of the brain are associated with memory and intelligence, functional deficit in these regions may cause loss of memory and intelligence. Although the process of impairment in neuronal signaling is still controversial, senile plaques and neurofibrillary tangles (NFT) are considered as main pathological causes.

In particular, development of senile plaques due to the accumulation of amyloid beta (Aβ) is a notable feature of this disease, and Alzheimer's disease can be confirmed by post-mortem examination (Khachaturian, *Arch. Neurol.* 42(11): 1097-105 (1985)).

As a way of treating Alzheimer's disease, a method of increasing the amount of acetylcholine to inhibit the impairment of cholinergic signaling or causing acetylcholine to act more effectively on transmission of neuronal cells has been proposed. Thus, patients with Alzheimer's disease use a variety of compounds for increasing the activity of acetylcholine.

Currently, the most effective way is to rapidly decompose acetylcholine in synapses, thus inhibiting the activity of acetylcholinesterase that prevents neuronal signaling. These inhibitors (e.g., tacrine, donepezil, galantamine and rivastigmine) are approved by the United States Food and Drug Administration (FDA) and are currently available on the market as Alzheimer's disease medications. Despite their effectiveness in preventing further destructive progress of this disease, they are not used to cure the disease.

Some compounds are aimed at improving the general state of neurons and maintaining aged cells in good function. For example, some drugs such as NGF or estrogen act as neuroprotecting agents to delay neurodegeneration, and other drugs such as antioxidants decrease cell damage caused by oxidation of cells resulting from normal aging.

Alzheimer's disease becomes serious as the amyloid beta peptide is accumulated in the neuritic space. It is thought that the progress of Alzheimer's disease can be delayed by reducing the accumulation of amyloid beta. In addition, amyloid precursor protein (APP) is considered to play a role in combination with proteinases in cells, such as α-, β- and γ-secretases. However, because the process of amyloid beta formation has not been fully elucidated scientifically, it is not yet possible to control the formation of amyloid beta.

It is not certain how the accumulation of amyloid beta acts on neuronal signaling. Abnormally cleaved APP induces amyloid beta generation, and plaque formation is induced by the accumulation of amyloid beta in the neuritic space. Thus, various factors involved in this cleavage reaction (e.g., inflammation reaction, etc.) increase the phosphorylation of tau protein, and also increase the accumulation of paired helical filaments (PHF) in combination with NFT, resulting in damage to the nerve. All these factors induce dysfunction of the nerve and, ultimately, accelerates the progress of Alzheimer's disease to dementia.

ELAVL2, or ELAVL-like neuron-specific RNA binding protein 2, is a type of nELAVL2. nELAVL2 is an RNA-binding protein expressed specifically in the brain and is known to be associated with neurodegenerative diseases. As a result of conducting high-throughput RNA sequencing using brain tissue after post-mortem of patients with Alzheimer's disease, it was found out that ELAVL2 was expressed with low levels.

In this regard, U.S. Pat. No. 5,532,219 discloses a composition for treating Alzheimer's disease containing 4,4'-diaminodiphenylsulfone, etc., U.S. Pat. No. 5,506,097 discloses a composition for treating Alzheimer's disease containing para-amidinophenylmethanesulfonyl fluoride or ebelactone A, and U.S. Pat. No. 6,136,861 discloses a composition for treating Alzheimer's disease containing bicyclo[2.2.1]heptane.

Recently, the development of therapeutic agents using a microRNA inhibitor is being attempted. WO 2013/045652 (Apr. 4, 2013) discloses a treatment of epilepsy using a miR-134 inhibitor, and WO 2015/025995 (Feb. 26, 2015) discloses treatment of epilepsy using a miR-203 inhibitor. In addition, European Patent Registration No. 2436784 (Sep. 11, 2013) discloses diagnosis and treatment of colon cancer using miR-203.

Although the development of therapeutic methods to reduce the effect of Alzheimer's disease is carried out actively, temporary improvement of symptoms is the current strategy. In conclusion, the current treatment of Alzheimer's disease is just focused on improvement of symptoms instead of slowing or reversing the progress of the disease. Despite the biological knowledge about the disease, clinical application is still not successful.

Thus, the inventors of the present disclosure have made efforts to develop an agent for preventing or treating brain diseases including Alzheimer's disease. As a result, they have confirmed that the inhibition of miR-485-3p expression or the inhibition of interaction between miR-485-3p and ELAVL2 leads to inhibition of Aβ42 production, inhibition of APP expression or inhibition of tau protein phosphorylation, thereby being useful in treating brain diseases, and have completed the present disclosure.

The information described in the Background section is only to enhance the understanding of the background of the present disclosure, and the information forming the prior art already known to those having ordinary skill in the art to which the present disclosure belongs may not be included.

SUMMARY OF THE DISCLOSURE

The present disclosure is directed to providing a pharmaceutical composition for preventing or treating a brain disease using a microRNA. The present disclosure is also directed to providing a method for screening an agent for preventing or treating a brain disease by measuring the expression level of a microRNA.

In order to achieve the above-described objects, the present disclosure provides a pharmaceutical composition for preventing or treating a brain disease, which contains a miR-485-3p inhibitor.

The present disclosure also provides a method for preventing or treating a brain disease, which includes a step of administering a pharmaceutically effective amount of a miR-485-3p inhibitor.

The present disclosure also provides a use of a miR-485-3p inhibitor for preventing or treating a brain disease.

The present disclosure also provides a use of a miR-485-3p inhibitor for preparing a medication for preventing or treating a brain disease.

The present disclosure also provides a method for screening an agent for preventing or treating a brain disease, which includes: (A) a step of treating a cell expressing miR-485-3p with a candidate substance and measuring the expression level of miR-485-3p; and (B) a step of screening the candidate substance as an agent for preventing or treating a brain disease if the expression level of miR-485-3p measured in the step (A) is decreased as compared to a control group not treated with the candidate substance.

BRIEF DESCRIPTION OF DRAWINGS

FIG. 4 shows a list of the 3'-untranslated region (UTR) mRNAs of ELAVL2.

Figure 1:
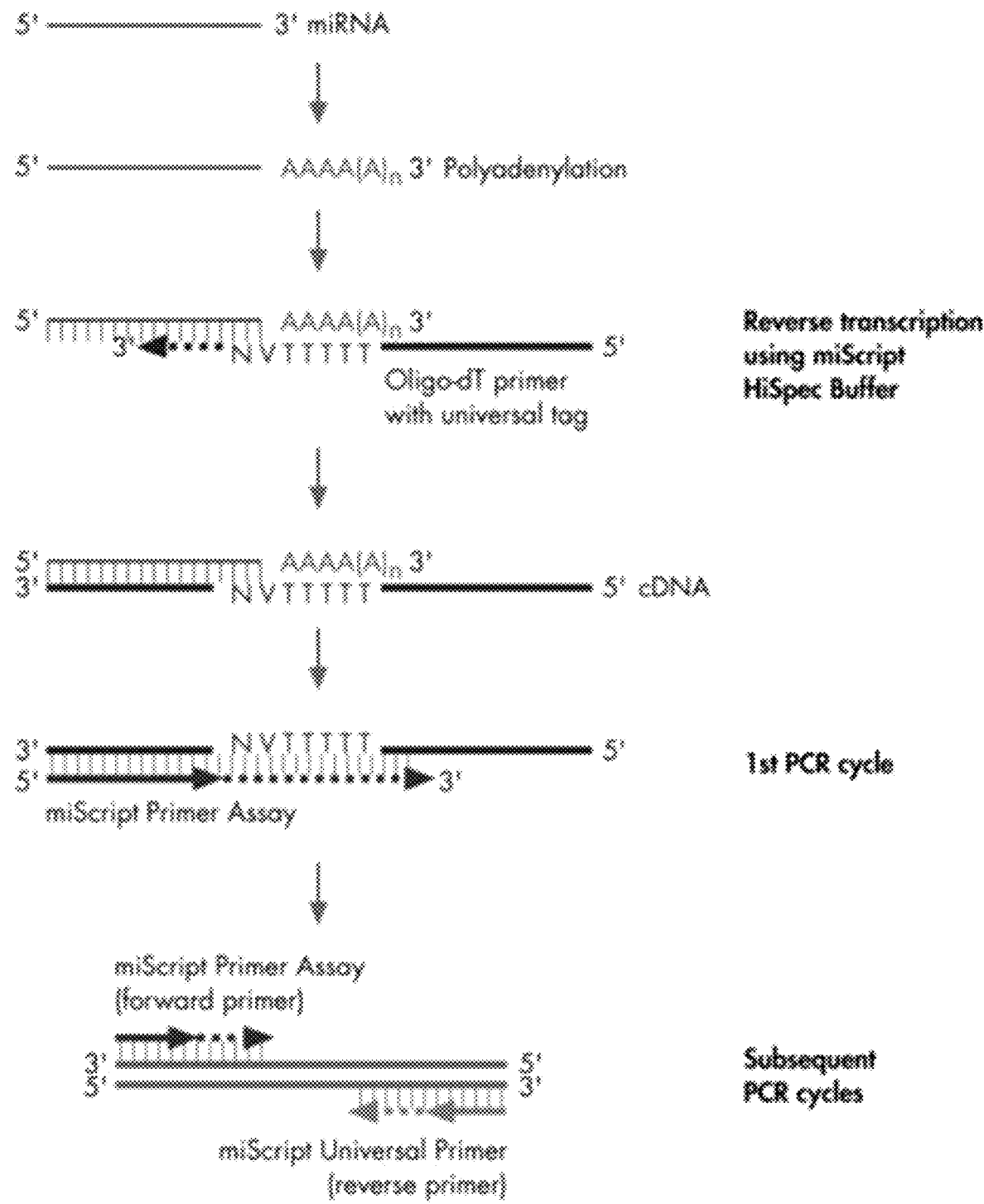
FIG. 1 summarizes a procedure of cDNA synthesis and detection.

Unless defined otherwise, all technical and scientific terms used herein have the same meaning as commonly understood by the skilled experts in the art to which the present disclosure belongs. In general, the nomenclature used herein is known well and commonly used in the art.

In a specific example of the present disclosure, it was confirmed that the expression of miR-485-3p is increased in Alzheimer's patients and that the expression level of ELAVL2 can be recovered and the production of Aβ 42 can be decreased through an oligonucleotide inhibiting the expression or activity of miR-485-3p, thereby improving behavioral disorder and decline in cognitive function, which are the main symptoms of Alzheimer's disease.

Accordingly, in an aspect, the present disclosure relates to a pharmaceutical composition for preventing or treating a brain disease, which contains a miR-485-3p inhibitor.

In the present disclosure, the 'miR' or 'microRNA (miRNA)' refers to a non-coding RNA consisting of 21-23 nucleotides, which is known to be involved in post-transcriptional regulation of gene expression by suppressing the translation of target RNA or promoting degradation thereof.

In the present disclosure, the mature sequence of the miRNA can be obtained from the miRNA database (http://www.mirbase.org). As of Aug. 13, 2012, 25,141 mature miRNAs derived from 193 species are listed in the miRNA database (19th edition, miRBase).

In general, following transcription into a precursor called a pre-miRNA, which has a hairpin structure and is about 70-80 nt (nucleotides) in length, a mature form of miRNA is produced as the pre-miRNA is cleaved by the RNAse III enzyme Dicer. The miRNA forms a ribonucleoprotein complex called a miRNP and cleaves a target gene or inhibits its translation through complementary binding to the target site. 30% or more of human miRNAs exist in the form of a cluster.

In the present disclosure, the miR-485-3p may be expressed in the brain, particularly in the hippocampus and the cortex, although not being limited thereto. By binding to the 3'-untranslated region of ELAVL2 mRNA which encodes ELAVL2 (ELAV-like RNA binding protein 2), it inhibits its expression, thereby lowering the concentration of the ELAVL2 protein in the brain.

In the present disclosure, the sequence of miR-485-3p may be derived from a mammal, for example, a human, mouse or rat. In an exemplary embodiment of the present disclosure, the sequence of miR-485-3p is derived from a human, and includes not only a mature sequence [5'-GUCAUACACGGCUCUCCUCUCU-3' (SEQ ID NO 1)] but also a precursor sequence [5'-ACUUG-GAGAGAGGCUGGCCGUGAUGAAUUCGAUUCAU-CAAAGCGAGUCAUAC ACGGCUCUCCUCUC-UUUUAGU-3' (SEQ ID NO 2)].

In the present disclosure, the miR-485-3p inhibitor may inhibit the expression of miR-485-3p. Alternatively, it may inhibit the interaction between miR-485-3p and the 3'-UTR of ELAVL2 (ELAV-like neuron-specific RNA binding protein 2).

In the present disclosure, the miR-485-3p inhibitor may inhibit or interfere with the action or function of miR-485-3p in cells. The inhibition of miR-485-3p includes direct inhibition of binding of miR-485-3p to its target, e.g., an mRNA molecule encoding the ELAVL2 protein. Also, direct inhibition of the function of miR-485-3p using a small molecule inhibitor, an antibody or an antibody fragment, or indirect regulation using an inhibitor or a small interfering RNA molecule is included.

In the present disclosure, the miR-485-3p inhibitor may be a nucleic acid molecule binding to all or a part of the base sequence of SEQ ID NO 1 or SEQ ID NO 2.

In the present disclosure, the nucleic acid molecule binding to a part of the base sequence of SEQ ID NO 1 or SEQ ID NO 2 may be 7-50 nt (nucleotides), specifically 10-40 nt, more specifically 15-30 nt, further more specifically 15-25 nt, particularly 16-19 nt, in length, although not being limited thereto.

In the present disclosure, the nucleic acid molecule may bind to the 1st or 2nd through the 7th or 8th base sequence of SEQ ID NO 1.

In the present disclosure, the nucleic acid molecule may be selected from a group consisting of DNA, RNA, an antagomir (antisense oligonucleotide of miRNA), siRNA, shRNA and an oligonucleotide.

In an exemplary embodiment of the present disclosure, the activity of the precursor sequence (SEQ ID NO 2) and the mature sequence (SEQ ID NO 1) is inhibited directly or indirectly for the interference with or inhibition of the activity of miR-485-3p. Also, the inhibition of the activity of miR-485-3p includes lowering its cellular level by inhibiting the transcription of miR-485-3p and/or the binding of miR-485-3p to its target mRNA.

In the present disclosure, the miR-485-3p inhibitor includes any substance capable of inhibiting the expression and/or activity of miR-485-3p. The substance includes a low-molecular-weight compound, an antagomir, an antisense molecule, a small hairpin RNA (shRNA) molecule, a small interfering RNA (siRNA) molecule, a seed target LNA (locked nucleic acid) oligonucleotide, a decoy oligonucleotide, an aptamer, a ribozyme, or an antibody that recognizes a DNA: RNA hybrid, although not being limited thereto.

In the present disclosure, the miR-485-3p inhibitor may be an antisense oligonucleotide which can inhibit the activity of miR-485-3p by complementarily binding to all or a part of the precursor and/or mature sequence, particularly the seed sequence.

The 'seed sequence' is a sequence which is very important in recognition of the target molecule of miRNA and is conserved in a variety of species (Krenz, M. et al., *J. Am. Coll. Cardiol.* 44: 2390-2397 (2004); H. Kiriazis, et al., *Annu. Rev. Physiol.* 62: 321 (2000)). Because miRNA binds to its target via the sequence seed, the translation, etc. of the target mRNA may be inhibited effectively by inhibiting the interaction between the seed sequence and the target.

In the present disclosure, the nucleic acid molecule may be an antisense oligonucleotide containing a sequence all or a part of which is complementary to the base sequence of SEQ ID NO 1. The antisense oligonucleotide may be represented by a base sequence selected from a group consisting of SEQ ID NO 3 to SEQ ID NO 7.

In the present disclosure, the antisense oligonucleotide may include a sequence all or a part of which is complementary to the 1st or 2nd through the 7th or 8th base sequence of the base sequence of SEQ ID NO 1, although not being limited thereto. The antisense oligonucleotide may be represented by a base sequence selected from a group consisting of 5'-GUGUAUGAC-3' (SEQ ID NO 3), 5'-UGUAUGAC-3' (SEQ ID NO 4), 5'-GUGUAUGA-3' (SEQ ID NO 5), 5'-UGUAUGA-3' (SEQ ID NO 6) or 5'-AGAGAGGAGAGCCGUGUAUGAC-3' (SEQ ID NO 7).

The antisense oligonucleotide includes a nucleic acid-based molecule having a sequence complementary to all or a part of a target miRNA, particularly the seed sequence of the miRNA, and thus capable of forming a duplex with the miRNA. Thus, the antisense oligonucleotide may be referred to as a complementary nucleic acid-based inhibitor.

In addition, the antisense oligonucleotide includes a variety of molecules, for example, a ribonucleic acid (RNA), a deoxyribonucleic acid (DNA), an antagomir, a 2'-O-modified oligonucleotide, a phosphorothioate-backbone deoxyribonucleotide, a phosphorothioate-backbone ribonucleotide, a PNA (peptide nucleic acid) oligonucleotide or an LNA (locked nucleic acid) oligonucleotide. Specifically, it may be a ribonucleic acid.

The ribonucleic acid includes a double-stranded small hairpin RNA (shRNA) molecule, a small interfering RNA (siRNA) molecule and a ribozyme.

The LNA has a locked conformation due to further modification between the 2' and 4' carbon of the ribose moiety of the oligonucleotide and, thus, ensures thermal stability.

The PNA (peptide nucleic acid) contains a peptide-based backbone instead of a sugar-phosphate backbone.

The 2'-O-modified oligonucleotide is specifically a 2'-O-alkyl oligonucleotide, more specifically a 2'-O—$C_{1-3}$ alkyl oligonucleotide, and most specifically a 2'-O-methyl oligonucleotide.

The antisense oligonucleotide includes an antisense oligonucleotide in a narrow sense, an antagomir and an inhibitory RNA molecule.

The antagomir is a chemically modified single-stranded oligonucleotide and is used to silence an endogenous microRNA. The antagomir contains a sequence that is not complementary at the Argonaute 2 (Ago2) cleavage site, or inhibits cleavage of Ago2 such that the base is modified with, for example, a 2-' methoxy group, a 3'-cholesterol group or a phosphorothioate. There is a complementary sequence to the target sequence.

In the present disclosure, the antagomir has a sequence which is at least partially or completely complementary to miR-485-3p. The antagomir may include one or more modification (e.g., 2'-O-methyl-sugar modification or 3'-cholesterol modification).

Alternatively, the antagomir may contain one or more phosphorothioate linkage and have a phosphorothioate backbone at least in part.

In the present disclosure, the appropriate length of the antagomir for inhibiting the expression of miR-485-3p is 7-50 nt (nucleotides), specifically 10-40 nt, more specifically 15-30 nt, more specifically 15-25 nt, more specifically 16-19 nt, although not being limited thereto.

The term 'complementary' as used the present disclosure means that the antisense oligonucleotide is sufficiently complementary to the miR-485-3p target under predetermined hybridization conditions or annealing conditions, specifically under physiological conditions, such that it can selectively hybridize to the target, and encompasses both partially or substantially complementary and completely (perfectly) complementary. Specifically, it means being completely complementary. Substantially complementary means that, although not completely complementary, it has complementarity sufficient to bind to the target sequence and exert an effect according to the present disclosure, i.e., interference with the activity of miR-485-3p.

The 'nucleic acid' includes an oligonucleotide, a DNA, an RNA, a polynucleotide, and analogs and derivatives thereof. For example, a PNA or a mixture thereof is included. In addition, the nucleic acid may be single- or double-stranded and can encode molecules including an mRNA, a microRNA, a siRNA, a polypeptides, etc.

In the present disclosure, the antisense oligonucleotide may include one or more modification selected from: 1) modification to a LNA (locked nucleic acid) or PNA (peptide nucleic acid) form; 2) substitution of the —OH group at the 2' carbon of a nucleotide with —CH$_3$ (methyl); and 3) modification of a nucleotide bond to phosphorothioate.

One or more nucleotide constituting the antisense oligonucleotide may be a LNA or a PNA. The sugar of at least one nucleotide constituting the same may be 2'-O-methylated or methoxylated, or one or more phosphothioate may be contained in the backbone, although not being limited thereto.

In the present disclosure, the miR-485-3p inhibitor may have one or more of the following features: 1) recovery of the expression level of ELAVL2; 2) inhibition of the production of amyloid beta 42 (Aβ42); 3) inhibition of the expression of amyloid precursor protein (APP); and 4) inhibition of the phosphorylation of tau protein.

In an example of the present disclosure, it was confirmed that the miR-485-3p inhibitor has the features of recovery of the expression level of ELAVL2, inhibition of the production of Aβ42, inhibition of the expression of APP and inhibition of the phosphorylation of tau protein using 5×FAD mouse, which is an animal model of Alzheimer disease which exhibits severe accumulation of intraneuronal Aβ42 from about 6 weeks due to overexpression of mutant forms of APP and PSEN1.

It is known that the decreased expression level of ELAVL2 is associated with the onset of Alzheimer's disease, autism spectrum disorder, mental retardation and amyotrophic lateral sclerosis. Especially, it is known that the level of the ELAVL2 protein is decreased by substances inducing excitotoxicity such as kainic acid, NMDA, quisulate, AMPA, glutamate, etc., resulting in neuronal cell death and disturbance of brain function, causing a number of brain diseases such as seizure, stroke, Parkinson's disease, spinal cord injury, etc. (Kaminska, B. et al., *Acta Biochim Pol.* 44: 781-789). Therefore, the recovery of the ELAVL2 protein through the inhibition of the activity of miR-485-3p can be used in the treatment of various brain diseases such as Alzheimer's disease, autism spectrum disorder, mental retardation, amyotrophic lateral sclerosis, seizure, stroke, Parkinson's disease, spinal cord injury, etc.

In the present disclosure, the brain disease may be selected from a group consisting of Alzheimer's disease, autism spectrum disorder, mental retardation, amyotrophic lateral sclerosis, seizure, stroke, Parkinson's disease and spinal cord injury, although not being limited thereto.

In the present disclosure, the pharmaceutical composition may further contain, in addition to the miR-485-3p inhibitor, one or more active ingredient exhibiting the same, similar or synergistic function for the treatment of related diseases or a compound which maintains/increases the solubility and/or absorbency of the miR-485-3p inhibitor or the active ingredient. And, optionally, it may further contain an immunomodulator and/or a chemotherapeutic agent.

The pharmaceutical composition may further contain one or more pharmaceutically acceptable diluent, carrier and/or adjuvant in addition to the above-mentioned active ingredient. As the pharmaceutically acceptable carrier, saline, sterile water, Ringer's solution, buffered saline, dextrose solution, maltodextrin solution, glycerol, ethanol, liposome, and a mixture of one or more of these components may be used. If necessary, other common additives such as an antioxidant, a buffer, a bacteriostatic agent, etc. may be added.

In addition, it can be formulated into an injectable formulation such as an aqueous solution, a suspension, an emulsion, etc., a pill, a capsule, a granule or a tablet by additionally adding a diluent, a dispersant, a surfactant, a binder and a lubricant, and it can be used by binding a target organ-specific antibody or other ligand with the carrier.

Furthermore, it can be suitably formulated depending on the particular disease or ingredient by using appropriate methods in the art or using the methods disclosed in the Remington's literature (Remington's Pharmaceutical Science (newest edition), Mack Publishing Company, Easton Pa.). For example, it can be formulated into one of a suspension, a liposomal formulation, an emulsion, a tablet, a capsule, a gel, a syrup or a suppository.

The pharmaceutical composition may be prepared into a suspension using an aqueous, nonaqueous or mixed medium. An aqueous suspension may further contain a material increasing the viscosity of the suspension, such as sodium carboxymethyl cellulose, sorbitol and/or dextran.

In the present disclosure, the pharmaceutical composition may be formulated into a formulation for intranasal administration, intravenous administration, subcutaneous injection, intrathecal injection, inhalation administration or oral administration.

The administration method of the pharmaceutical composition according to the present disclosure is not particularly limited and any known administration method of inhibitors may be applied. Depending on purposes, parenteral administration (e.g., intranasal, intravenous, subcutaneous, intraperitoneal or topical administration) or oral administration may be employed. Specifically, administration by intranasal injection may be selected to achieve a quick therapeutic effect.

The pharmaceutical composition may be delivered via various routes, e.g., via infusion, bolus injection, transdermal or transmucosal administration (via buccal, anal or intestinal mucosa), or systemic or topical administration.

In the present disclosure, the pharmaceutical composition may be delivered to the brain. Specifically, the pharmaceutical composition may be introduced to the central or peripheral nerves via an appropriate route. The appropriate route includes intraventricular or intrathecal administration. The administration may be achieved using a catheter connected to a reservoir. Also, the pharmaceutical composition may be formulated as an aerosol and may be administered to the lungs using an inhaler or a nebulizer. However, the appropriate route is not limited as long as the effect of the present disclosure is achieved, and includes intravenous administration, subcutaneous injection, intrathecal injection, inhalation administration or oral administration.

In the present disclosure, the pharmaceutical composition can be prepared into a variety of unit dosage forms. Such forms include a nasal drop, a nasal spray, a nasal gel, a nasal ointment and a nasal powder, although not being limited thereto.

In an exemplary example of the present disclosure, the composition could be administered intranasally. The effect of the pharmaceutical composition can be enhanced when it is administered intranasally because it is delivered to the brain through the olfactory pathway. The nasal cavity refers to a space in the nose, which is divided into left and right fossae by the nasal septum, and the intranasal administration refers to delivery of the composition of the present disclosure to any tissue of the nasal epithelium. For the intranasal administration, an intranasally acceptable carrier may be contained. The carrier refers to one or more solid or liquid filler, diluent or encapsulating material which is suitable for administration to any portion of the nasal epithelium of a mammal, specifically human. Typically, the carrier may be a liquid, a solution, a suspension, a gel, an ointment, a lotion, or a combination thereof. Specifically, the carrier may be a pharmaceutically acceptable aqueous carrier.

In addition, the carrier may contain a delivery-enhancing agent. An intranasal delivery-enhancing agent may include an aggregation-inhibiting agent, a dosage-changing agent, a pH control agent, a degradative enzyme-inhibiting agent, a mucolytic or mucus-clearing agent, a ciliostatic agent, a membrane penetration-enhancing agent, a surfactant, a bile salt, a phospholipid or fatty acid additive, a mixed micelle, a liposome or carrier, an alcohol, an enamine, a nitric oxide-donating compound, a long-chain amphiphilic molecule, a small hydrophobic penetration enhancer, a sodium or salicylic acid derivative, a glycerol ester of acetoacetic acid, a cyclodextrin or beta-cyclodextrin derivative, a medium-chain fatty acid, a chelating agent, an amino acid or a salt thereof, a N-acetylamino acid or a salt thereof, a degradative enzyme for a selected membrane component, a fatty acid synthesis inhibitor, a cholesterol synthesis inhibitor, a nitric oxide-stimulating material, a modulatory agent of epithelial junction physiology such as chitosan or a chitosan derivative, a vasodilator, a selective transport-enhancing agent, etc. In order to enhance intranasal mucosal delivery, a stabilizing delivery vehicle, carrier, support, complex-forming species, etc. which allows effective combination, association, storage and encapsulation of the composition of the present disclosure and stabilizes the active ingredient may be contained.

In the present disclosure, the pharmaceutical composition may be administered in a pharmaceutically or therapeutically effective amount. The pharmaceutically or therapeutically effective amount means an amount sufficient to treat a disease at a reasonable benefit/risk ratio applicable to medical treatment, and an effective dose level will depend on factors including the type and severity of the disease, the activity of a drug, sensitivity to the drug, the time of administration, the route of administration, the rate of excretion, the duration of the treatment, and drugs used together, and other factors well known in the medical field.

In addition, the pharmaceutical composition may be administered as an individual therapeutic agent or in combination with other therapeutic agents, sequentially or concurrently with conventional therapeutic agents, and may be administered singly or multiply. It is important that the pharmaceutical composition is administered in such an amount that the maximum effect can be obtained with a minimum amount without side effects considering all of the above-mentioned factors, which can be easily determined by those skilled in the art.

The dosage may vary depending on the patient's body weight, age, sex, health condition and diet, administration time, administration method, excretion rate, the severity of the disease, etc., and a proper dosage may also vary depending on the amount of the drug accumulated in the patient's body and/or the specific efficacy of the polynucleotide used. In general, it can be calculated on the basis of $EC_{50}$ measured as effective from an in-vivo animal model and in vitro. For example, it may be from 0.01 µg to 1 g per 1 kg of body weight, and may be administered once to several times per unit period in a daily, weekly, monthly, or annual unit period. Also, it can be administered continuously for a long period of time using an infusion pump. The number of repeated administrations is determined in consideration of the time during which the drug remains in the body, the drug concentration in the body, and the like. Even after treatment according to the course of disease treatment, the pharmaceutical composition can be continuously administered to prevent the recurrence of the disease.

In the present disclosure, the active ingredient of the pharmaceutical composition, e.g., the antisense oligonucleotide, can be used in the composition as it is or in the form of a pharmaceutically acceptable salt. The pharmaceutically acceptable salt refers to a salt that retains the desired biological activity of the oligonucleotide according to the present disclosure and exhibits minimal undesired toxicological effect. The salt includes, for example, a base addition salt formed with a metal cation such as zinc, calcium, bismuth, barium, magnesium, aluminum, copper, cobalt, nickel, cadmium, sodium, potassium, etc., or a salt formed with a cation derived from ammonia, N,N-dibenzylethylenediamine, D-glucosamine, tetraethylammonium or ethylenediamine, although not being limited thereto.

In the present disclosure, the antisense oligonucleotide, which is the active ingredient of the pharmaceutical composition, may be negatively charged due to the characteristic of the nucleotide. The cellular uptake of the antisense oligonucleotide may be reduced due to the lipophilic nature of cell membranes. The hindered uptake due to polarity can be avoided by using the prodrug approach described in Crooke, R. M. (1998) in Crooke, S. T. Antisense research and Application. Springer-Verlag, Berlin, Germany, vol. 131, pp. 103-140.

The term 'improvement', 'treatment', or 'alleviation' as used in the present disclosure means any action to change favorably or improve the symptoms of related diseases by administering the composition. Those of ordinary skill in the art to which the present disclosure belongs will know the exact criteria of diseases by referring to the data presented, for example, by the Korean Academy of Medical Sciences and will be able to judge the degree of improvement, progress and treatment.

The term "prevention" used in the present disclosure means any action to inhibit or delay the onset of related diseases. It will be apparent to those skilled in the art that the related diseases can be prevented if the pharmaceutical composition according to the present disclosure is administered when or before early symptoms appear.

In an example of the present disclosure, it was confirmed that the expression of miR-485-3p is increased in Alzheimer's patients and that behavioral disorder and decline in cognitive function, which are the main symptoms of Alzheimer's disease, can be improved by an oligonucleotide which inhibits the expression or activity of miR-485-3p.

Accordingly, in another aspect, the present disclosure relates to a method for preventing or treating a brain disease, which includes a step of administering a pharmaceutically effective amount of a miR-485-3p inhibitor.

In the present disclosure, the method for preventing or treating a brain disease inhibits the activity of miR-485-3p in the cells or tissues, particularly in the brain cells or brain tissues, of a subject.

In another aspect, the present disclosure relates to a use of a miR-485-3p inhibitor for preventing or treating a brain disease.

In another aspect, the present disclosure relates to a use of a miR-485-3p inhibitor for preparing a medication for preventing or treating a brain disease.

Reference can be made to the above description regarding the miR-485-3p inhibitor, the regulation or inhibition of the activity of miR-485-3p, administration method, diseases that can be treated, etc.

In another aspect, the present disclosure relates to a method for screening an agent for preventing or treating a brain disease, which includes: (A) a step of treating a cell expressing miR-485-3p with a candidate substance and measuring the expression level of miR-485-3p; and (B) a step of screening the candidate substance as an agent for preventing or treating a brain disease if the expression level of miR-485-3p measured in the step (A) is decreased as compared to a control group not treated with the candidate substance.

In the present disclosure, the activity of miR-485-3p may be determined by analyzing the interaction between miR-485-3p and the 3'-UTR of ELAVL2 (ELAV-like neuron-specific RNA binding protein 2).

In the present disclosure, the brain disease may be selected from a group consisting of Alzheimer's disease, autism spectrum disorder, mental retardation, amyotrophic lateral sclerosis, seizure, stroke, Parkinson's disease and spinal cord injury.

In the screening method of the present disclosure, after contacting a cell expressing miR-485-3p with candidate substances, the change in the expression level of miR-485-3p may be compared with that before the contacting or with a control group cell not in contact with the test substances and the substance which shows change, particularly decrease, in the expression level may be selected as an agent for preventing or treating a brain disease.

The expression level of miR-485-3p may be measured by performing a known method such as northern blot, RT-PCR, a hybridization method using a microarray, etc.

In the present disclosure, the miR-485-3p is provided in the form of a cell expressing the same, and the activity is determined by analyzing the interaction between miR-485-3p and the 3'-UTR of its target ELAVL2 protein. For example, after contacting a cell expressing the miR-485-3p according to the present disclosure with candidate substances, the change in the expression level of miR-485-3p may be compared with that before the contacting or with a control group cell not in contact with the test substances and the substance which shows change, particularly decrease, in the expression level may be selected as an agent for preventing or treating a brain disease.

In the present disclosure, the type of the cell and the amount and kind of the candidate substance used in the screening method will vary depending on the particular test method and candidate substance used, and those skilled in the art will be able to select the suitable type, amount and/or condition of the cell. Based on the test result, the substance which leads to decreased activity of miR-485-3p in the presence of the test substance as compared to the control group not in contact with the test substance is selected as a therapeutic agent. The decrease means decrease by about 99% or less, decrease by about 95% or less, decrease by about 90% or less, decrease by about 85% or less, decrease by about 80% or less, decrease by about 75% or less, decrease by about 70% or less, decrease by about 65% or less, decrease by about 60% or less, decrease by about 55% or less, decrease by about 50% or less, decrease by about 45% or less, decrease by about 40% or less, decrease by about 30% or less, or decrease by about 20% or less, as compared to the control group, although not being limited thereto.

The RNA-RNA interaction used in the screening method according to the present disclosure may be detected by a method known in the art, for example, RNA walk (Lusting et al., *Nucleic Acids Res.* 2010; 38 (1): e5) or yeast two-hybrid system (Piganeau et al, RNA 2006; 12: 177-184, and RNA: A Laboratory Manual (Cold Spring Harbor Laboratory Press 2011)).

The candidate substance means a substance which is expected to inhibit the activity of miR-485-3p, and includes a low-molecular-weight compound, a high-molecular-weight compound, a mixture of compounds (e.g., a natural extract or a cell or tissue culture), a biomedicine (e.g., a protein, an antibody, a peptide, DNA, RNA, an antisense oligonucleotide, RNAi, an aptamer, RNAzyme and DNAzyme), a sugar and a lipid, although not being limited thereto. The candidate substance can be a polypeptide having two or more amino acid residues, for example, 6, 10, 12, 20 or fewer, or more than 20, e.g., 50, amino acid residues. The candidate substance may be obtained from a library of synthetic or natural compounds, and a method for obtaining a library of such compounds is known in the art. The libraries of synthetic compounds are commercially available from Maybridge Chemical Co. (UK), Comgenex (USA), Brandon Associates (USA), Microsource (USA) and Sigma-Aldrich (USA), and the libraries of natural compounds are commercially available from Pan Laboratories (USA) and MycoSearch (USA). The test substance may be obtained by a variety of combinatorial library methods known in the art, for example, a biological library, a spatially addressable parallel solid-phase or solution-phase library, a synthetic library requiring deconvolution, a "one-bead/one-compound" library, and a synthetic library using affinity chromatography selection. Method for the synthesis of molecular libraries are disclosed in DeWitt et al., *Proc. Natl. Acad. Sci. U.S.A.* 90, 6909, 1993; Erb et al. *Proc. Natl. Acad. Sci. U.S.A.* 91, 11422, 1994; Zuckermann et al., *J. Med. Chem.* 37, 2678, 1994; Cho et al., Science 261, 1303, 1993; Carell et al., *Angew. Chem. Int. Ed. Engl.* 33, 2059, 1994; Carell et al., *Angew. Chem. Int. Ed. Engl.* 33, 2061; Gallop et al., *J. Med. Chem.* 37, 1233, 1994, or the like.

In the present disclosure, a low-molecular-weight compound exhibiting a therapeutic effect may be used for the screening purpose of a drug which treats a brain. For example, a compound with a molecular weight of about 1000 Da, e.g., 400 Da, 600 Da or 800 Da, may be used. Depending on purposes, these compounds can form a part of a compound library, and the number of compounds that make up the library can also vary from dozens to millions. The compound library may contain peptides, peptoids, other cyclic or linear oligomeric compounds, template-based low-molecular-weight compounds, e.g., benzodiazepines, hydantoins, biaryls, carbocycles and polycyclic compounds (e.g., naphthalene, phenothiazine, acridine, steroid, etc.), carbohydrates, amino acid derivatives, dihydropyridines, benzhydryls and heterocycles (e.g. triazine, indole, thiazolidine, etc.), although not being limited thereto.

Also, biologics may be used for the screening. The biologics refers to use of a cell or a biomolecule, and the biomolecule refers to a protein, a nucleic acid, a carbohydrate, a lipid or a material produced in vivo or in vitro using a cellular system. The biomolecule may be provided either alone or in combination with other biomolecules or cells. For example, the biomolecule includes polynucleotides, peptides, antibodies or other proteins or biological organic materials found in the plasma.

Hereinafter, the present disclosure will be described in detail through examples. However, the following examples are for illustrative purposes only and it will be apparent to those of ordinary skill in the art that the scope of the present disclosure is not limited by the examples.

EXAMPLE 1: ANALYSIS OF MIRNA EXPRESSION PATTERN IN ALZHEIMER'S PATIENTS USING MICROARRAY (1) Patients and Sample Preparation Table 1 shows the characteristics of the patients used in the study. About 3 mL of blood was collected in blood tubes (Becton Dickinson, Germany) containing sodium citrate (3.2% w/v) from 4 patients diagnosed with Alzheimer's dementia by physicians. Four healthy adults of corresponding ages (±4 years) were included as a control group.

TABLE 1

Sex and age of normal group and patient group

| Group | Sample No. | Sex | Age |
|---|---|---|---|
| Normal group | N1 | Female | 78 |
| Normal group | N2 | Male | 72 |
| Normal group | N3 | Female | 74 |
| Normal group | N4 | Male | 79 |
| Patient Group | S1 | Female | 72 |
| Patient Group | S2 | Female | 82 |
| Patient Group | S3 | Female | 84 |
| Patient Group | S4 | Male | 75 |

The blood was centrifuged for 10 minutes at 3,500 rpm to separate plasma and then stored at −80° C. until RNA extraction. miRNA was extracted using the miRNAeasy Serum/Plasma kit (Qiagen, USA) according to the manufacturer's recommendations. The concentration and purity of the extracted RNA were analyzed using Bioanalyzer 2100 (Agilent, USA). Eight groups including a normal group satisfied the quality criteria and were used in the study.

(2) Microarray Screening

Table 2 shows a list of genes used in microarray assay. The mature sequence of each miRNA is available from the miRNA database (http://www.mirbase.org). The extracted RNA was screened using a miRNA array containing 84 different miRNAs known to be associated with human neurological development and the progress of neurological disease.

TABLE 2

List of genes used in miRNA qPCR array assay

| No. | Mature miRNA list |
|---|---|
| 1 | hsa-let-7b-5p |
| 2 | hsa-let-7c-5p |
| 3 | hsa-let-7d-5p |
| 4 | hsa-let-7e-5p |
| 5 | hsa-let-7i-5p |
| 6 | hsa-miR-101-3p |
| 7 | hsa-miR-105-5p |
| 8 | hsa-miR-106b-5p |
| 9 | hsa-miR-107 |
| 10 | hsa-miR-124-3p |
| 11 | hsa-miR-125b-5p |
| 12 | hsa-miR-126-5p |
| 13 | hsa-miR-128-3p |
| 14 | hsa-miR-130a-3p |
| 15 | hsa-miR-132-3p |
| 16 | hsa-miR-133b |
| 17 | hsa-miR-134-5p |
| 18 | hsa-miR-135b-5p |
| 19 | hsa-miR-138-5p |
| 20 | hsa-miR-139-5p |
| 21 | hsa miR 140 5p |
| 22 | hsa-miR-146a-5p |
| 23 | hsa-miR-146b-5p |
| 24 | hsa-miR-148b-3p |
| 25 | hsa-miR-151a-3p |
| 26 | hsa miR 152 3p |
| 27 | hsa-miR-15a-5p |
| 28 | hsa-miR-15b-5p |
| 29 | hsa-miR-181a-5p |
| 30 | hsa-miR-181d-5p |
| 31 | hsa-miR-191-5p |
| 32 | hsa-miR-193b-3p |
| 33 | hsa-miR-195-5p |
| 34 | hsa-miR-19b-3p |
| 35 | hsa-miR-203a-3p |
| 36 | hsa-miR-20a-5p |
| 37 | hsa-miR-212-3p |
| 38 | hsa-miR-22-3p |
| 39 | hsa-miR-24-3p |
| 40 | hsa-miR-26b-5p |
| 41 | hsa-miR-27a-3p |
| 42 | hsa-miR-28-5p |
| 43 | hsa-miR-298 |
| 44 | hsa-miR-29a-3p |
| 45 | hsa-miR-29b-3p |
| 46 | hsa-miR-29c-3p |
| 47 | hsa-miR-302a-5p |
| 48 | hsa-miR-302b-5p |
| 49 | hsa-miR-30d-5p |
| 50 | hsa-miR-320a |
| 51 | hsa-miR-328-3p |
| 52 | hsa-miR-337-3p |
| 53 | hsa-miR-338-3p |
| 54 | hsa-miR-339-5p |
| 55 | hsa-miR-342-3p |
| 56 | hsa-miR-346 |
| 57 | hsa-miR-34a-5p |
| 58 | hsa-miR-376b-3p |
| 59 | hsa-miR-381-3p |
| 60 | hsa-miR-409-3p |
| 61 | hsa-miR-431-5p |
| 62 | hsa-miR-432-5p |
| 63 | hsa miR 433 3p |
| 64 | hsa-miR-455-5p |
| 65 | hsa-miR-484 |
| 66 | hsa-miR-485-3p |
| 67 | hsa-miR-485-5p |
| 68 | hsa miR 487a 3p |
| 69 | hsa-miR-488-3p |
| 70 | hsa-miR-489-3p |
| 71 | hsa-miR-499a-5p |
| 72 | hsa-miR-509-3p |
| 73 | hsa-miR-511-5p |
| 74 | hsa-miR-512-3p |
| 75 | hsa-miR-518b |
| 76 | hsa-miR-539-5p |
| 77 | hsa-miR-652-3p |
| 78 | hsa-miR-7-5p |
| 79 | hsa-miR-9-5p |
| 80 | hsa-miR-9-3p |
| 81 | hsa-miR-92a-3p |

TABLE 2-continued

List of genes used in miRNA qPCR array assay

| No. | Mature miRNA list |
|---|---|
| 82 | hsa-miR-93-5p |
| 83 | hsa-miR-95-3p |
| 84 | hsa-miR-98-5p |

FIG. 1 summarizes the procedure of cDNA synthesis and detection. The quantitative PCR assay method can be summarized as follows. A mature miRNA is generally a 22-nt, non-coding RNA and is responsible for post-transcriptional regulation. Polyadenylation of mature miRNA was induced by poly(A) polymerase, and cDNA was synthesized using oligo-dT primers. The oligo-dT primer enables the amplification of the mature miRNA during the real-time PCR process because it has a 3' degenerate anchor and a universal tag sequence at the 5' end. The mature miRNA was quantified during the real-time PCR process using the miScript SYBR Green PCR kit (Qiagen).

(3) Analysis of miRNA Expression Pattern Through Volcano Plot

Figure 2A:
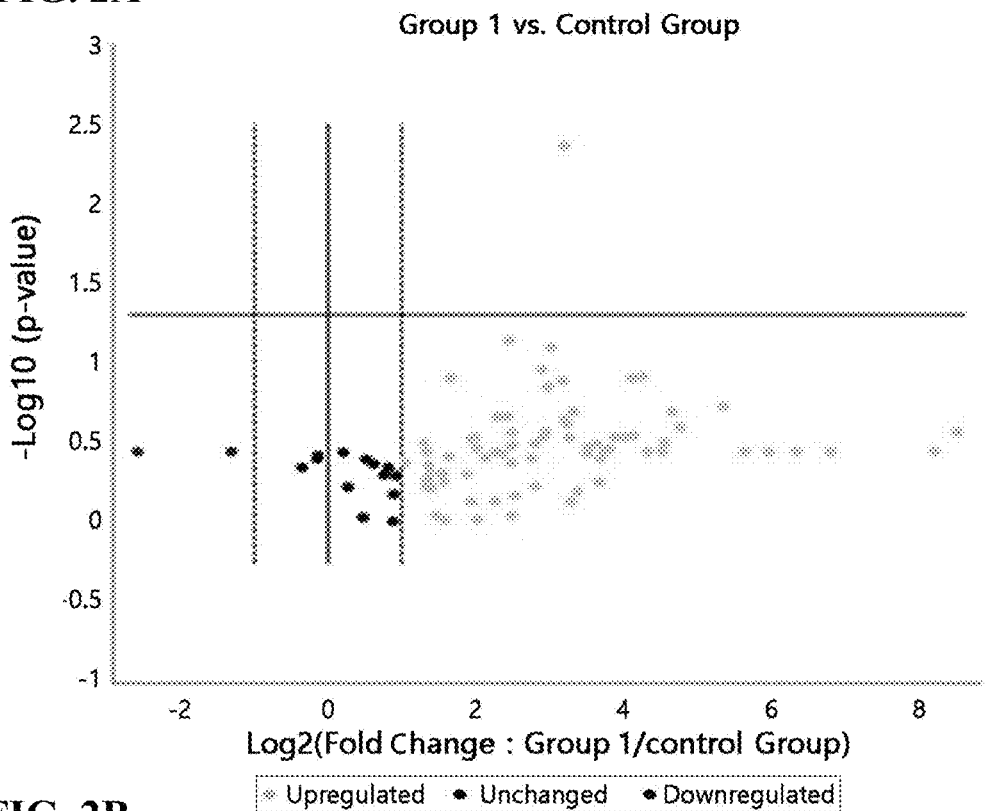
FIGS. 2A-2B show a miRNA expression pattern analysis result (volcano plot) for a patient group as compared to a normal group (FIG. 2A), and a miRNA expression pattern analysis result (scatter plot) for a patient group as compared to a normal group (FIG. 2B).
Figure 2B:
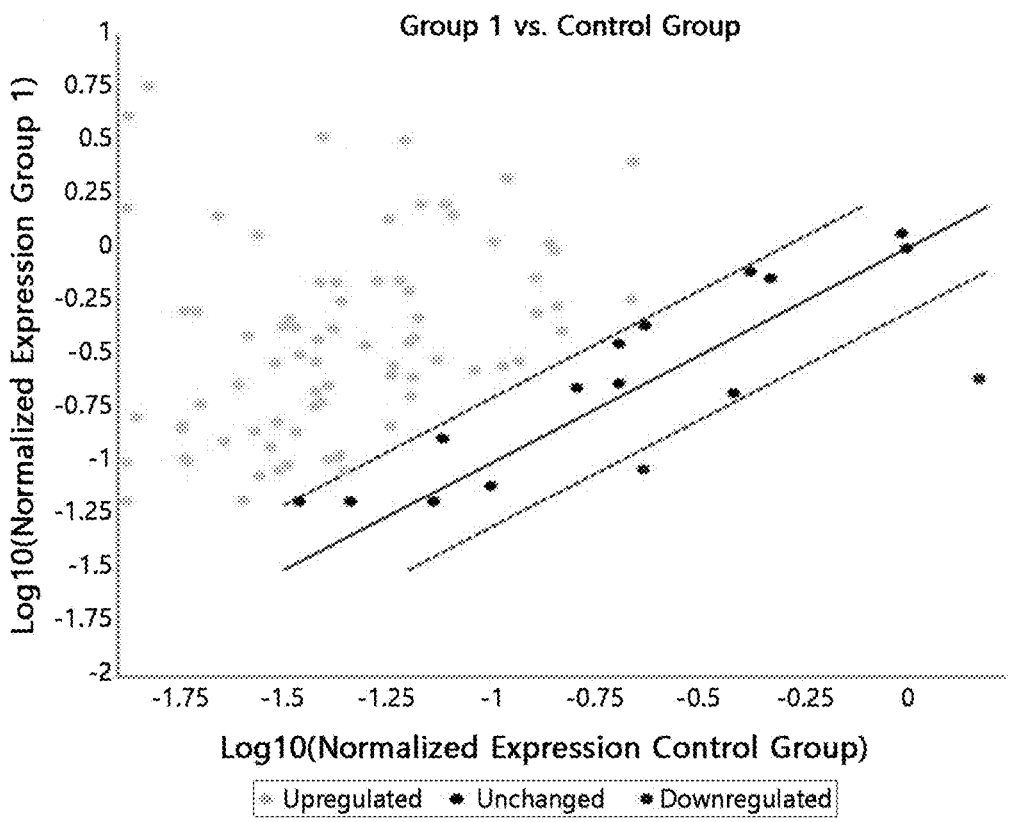

FIG. 2A shows a miRNA expression pattern analysis result (volcano plot) for the patient group as compared to the normal group, and FIG. 2B shows a miRNA expression pattern analysis result (scatter plot) for the patient group as compared to the normal group. The expression pattern of 84 miRNAs was analyzed as compared to the normal group.

The x axis represents fold-change and they axis represents−log 10 of the p value. The horizontal black line shows where the p value is 0.05 or smaller. As a result of the volcano plot analysis, it was confirmed that the expression of hsa-miR-105-5p, hsa-miR-98-5p, hsa-miR-15a-5p, hsa-miR-134-5p, hsa-miR-409-3p, hsa-miR-19b-3p, hsa-miR-92a-3p, hsa-miR-28-5p, hsa-miR-30d-5p, hsa-miR-212-3p, hsa-miR-93-5p, hsa-miR-342-3p, hsa-miR-381-3p, hsa-miR-431-5p, hsa-miR-130a-3p, hsa-miR-146b-5p, hsa-miR-29a-3p, hsa-miR-132-3p, hsa-miR-376b-3p, hsa-miR-22-3p, hsa-miR-509-3p, hsa-miR-139-5p, hsa-miR-499a-5p, hsa-miR-203a-3p, hsa-miR-95-3p, hsa-miR-128-3p, hsa-miR-487a-3p, hsa-miR-485-3p, hsa-miR-195-5p, hsa-miR-433-3p, hsa-miR-133b, hsa-miR-191-5p, hsa-miR-489-3p, hsa-miR-432-5p, hsa-miR-29c-3p, hsa-miR-485-5p, hsa-miR-652-3p, hsa-miR-126-5p, hsa-miR-328-3p, hsa-let-7b-5p, hsa-miR-539-5p, hsa-miR-106b-5p, hsa-miR-101-3p, hsa-miR-302a-5p, hsa-miR-484, hsa-miR-518b, hsa-miR-148b-3p, hsa-miR-181d-5p, hsa-miR-7-5p, hsa-miR-512-3p, hsa-miR-151a-3p, hsa-miR-15b-5p, hsa-let-7e-5p, hsa-miR-135b-5p, hsa-miR-181a-5p, hsa-miR-138-5p, hsa-miR-34a-5p, hsa-miR-346, hsa-miR-511-5p, hsa-miR-485-3p, hsa-miR-485-5p, hsa-miR-487a-3p, hsa-miR-489-3p, hsa-miR-499a-5p, hsa-miR-509-3p, hsa-miR-511-5p, hsa-miR-512-3p, hsa-miR-518b, hsa-miR-539-5p, hsa-miR-652-3p, hsa-miR-7-5p, hsa-miR-92a-3p, hsa-miR-93-5p hsa-miR-95-3p and hsa-miR-98-5p was increased in the patient group. However, the regulation of miRNA was not statistically significant except for hsa-miR-485-3p. The expression of hsa-485-3p was significantly increased as compared to the normal group, with a p value of 0.00439. Therefore, hsa-miR-485-3p can be used as a marker for treatment of Alzheimer's disease.

Table 3 shows the base sequence of has-miR-485-3p. Based on the above result, a functional study was conducted to elucidate the physiological functions of has-miR-485-3p on cells by synthesizing the sequence.

TABLE 3

Base sequence of hsa-miR485-3p

| Gene | Sequence (5'→3') | SEQ ID NO |
|---|---|---|
| hsa-miR485-3p | GUCAUACACGGCUCUCCUCUCU | 1 |

EXAMPLE 2: ANALYSIS OF MIR-485-3P EXPRESSION IN HIPPOCAMPUS AND CEREBRAL CORTEX OF 5×FAD MOUSE (RT-QPCR)

(1) Research Methods

The 5×FAD transgenic mouse is an animal model of Alzheimer disease obtained by overexpressing mutant forms of APP and PSEN1, which exhibits severe accumulation of intraneuronal Aβ42 from about 6 weeks.

Given the results of Example 1, RT-qPCR was performed to confirm the expression of miR-485-3p in the dementia animal model. 5×FAD transgenic mice and wild-type (WT) mice were deeply anesthetized and sacrificed by decapitation. After excising the brain immediately, the hippocampus and cerebral cortex were dissected from the remaining brain structure. Total miRNA was isolated from the hippocampus using the PAXgene Tissue miRNA kit (Qiagen, USA) according to the manufacturer's instructions. cDNA was synthesized using the miScript II RT kit (Qiagen, USA), and qPCR was performed using the mmu_miR-485-3p miScript Primer Assay kit and the miScript SYBR Green PCR kit. The miRNA level was quantified by normalizing to snoRNA202 (control mouse).

(2) Research Results

Figure 3:
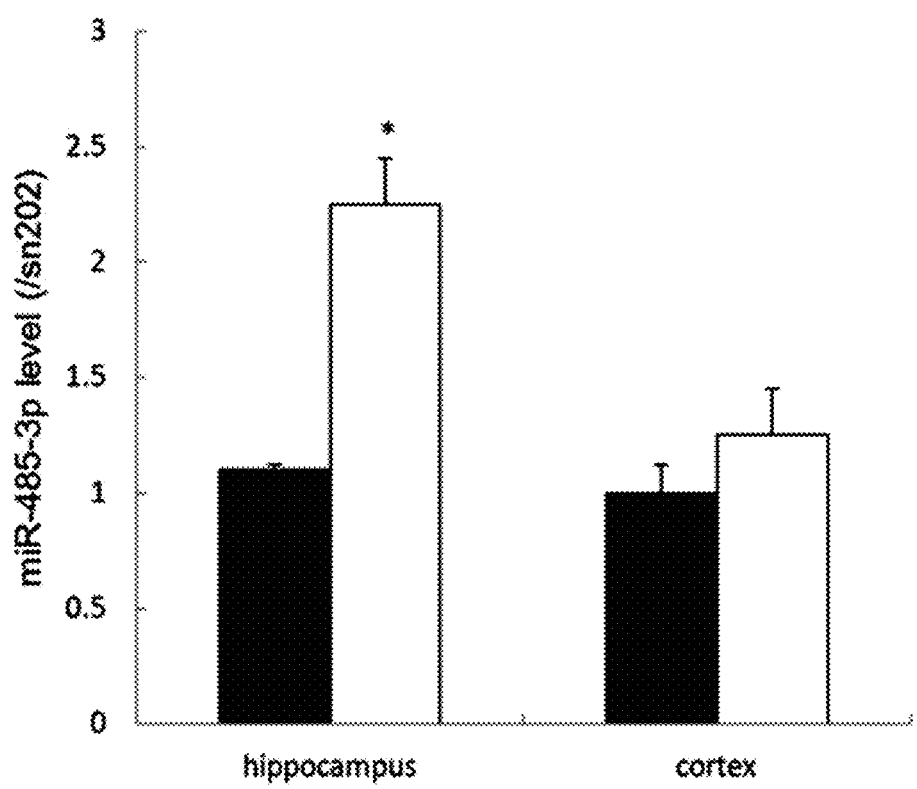
FIG. 3 compares the expression of miR-485-3p in the hippocampus and the cortex.

FIG. 3 compares the expression of miR-485-3p in the hippocampus and the cortex. RT-PCR was conducted to investigate the expression pattern of miR-485-3p in the hippocampus and the cerebral cortex of 5×FAD. The result showed that the expression of miR-485-3p was increased in the hippocampus of 5×FAD as compared to WT. This, together with the results of Example 1, shows that the expression of miR-485-3p is increased in Alzheimer's dementia. Therefore, the neuronal target mRNA or protein that may be affected by miR-485-3p was investigated.

EXAMPLE 3: PREDICTION OF TARGET GENE OF MIR-485-3P

In order to analyze the base sequence and target location of hsa-miR-485-3p, it was confirmed using a target prediction software (miRDB) that the 3'-untranslated region (UTR) of human-derived ELAVL2 is the target of hsa-miR-485-3p. It was confirmed that the identified seed sequence was conserved also in mmu-miR-485-3p and the 3'-untranslated region of mouse-derived ELAVL2.

FIG. 4 shows a list of the 3'-untranslated region (UTR) mRNAs of ELAVL2, and shows the target 3'-untranslated region (UTR) mRNAs of miR485-3p. The 5' seed sequence of miR-485-3p (ELAVL2) is shown in blue color. Table 4 shows the base sequence and target location of mmu-miR485-3p. It was confirmed using a target prediction software (miRDB) that the 3'-untranslated region (UTR) of human-derived ELAVL2 is the target of mmu-miR-485-3p.

TABLE 4

Analysis of base sequence and target location of mmu-miR485-3p

| Gene | Sequence (5' > 3') | 서열번호 |
|---|---|---|
| mmu-miR-485-3p | AGUCAUACACG GCUCUCCUCUC | SEQ ID NO |

| Target gene | Gene name | 3P-seq tags + 5 | Total sites | Representative miRNA |
|---|---|---|---|---|
| ELAVL2 | ELAV like neuron-specific RNA binding protein 2 | 78 | 3 | mmu-miR-485-3p |

EXAMPLE 4: CONFIRMATION OF EXPRESSION OF AMYLOID BETA (Aβ) 42 AND ELAVL2 IN HIPPOCAMPUS AND CEREBRAL CORTEX OF 5×FAD MOUSE (1) Research Methods Given the results of Example 3, the expression of Aβ 42 and ELAVL2 in the hippocampus and the cerebral cortex of 5×FAD was investigated. After sacrificing an anesthetized mouse by decapitation, the brain was extracted immediately. After preparing a homogenate of the brain (hippocampus and cerebral cortex), western blot was conducted using anti-ELAVL2 antibody (Abcam, USA). The immunoreactive protein was visualized with a chemiluminescence reagent (GE Healthcare, UK) and was measured and quantified using a chemiluminescence analyzer (Fusion SL). Aβ 42 in the hippocampus and the cerebral cortex was quantified by using the mouse/rat amyloid beta (1-42) ELISA kit (IBL) according to the manufacturer's instructions.

(2) Research Results

1) Confirmation of Aβ 42 Expression in Hippocampus and Cerebral Cortex

Figure 5A:
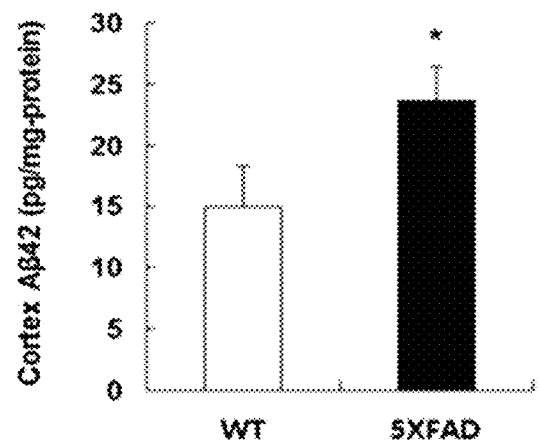
FIGS. 5A-5B shows a comparative quantitative analysis result of Aβ 42 in the cerebral cortex of 5×FAD (FIG. 5A), and a comparative quantitative analysis result of Aβ 42 in the hippocampus (FIG. 5B).
Figure 5B:
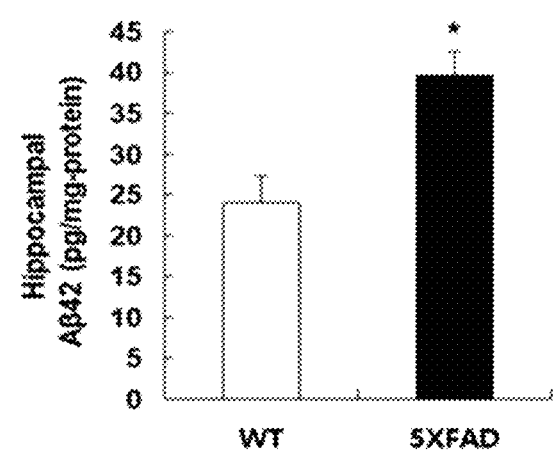

FIGS. 5A-5B show results of quantitatively comparing the expression of Aβ42 in the cerebral cortex (FIG. 5A) and the hippocampus (FIG. 5B) of 5×FAD. It was confirmed that Aβ42 was significantly increased as compared to wild-typ (WT) both in the cerebral cortex and in the hippocampus.

2) Confirmation of ELAVL2 Expression in Hippocampus and Cerebral Cortex

Figure 6:
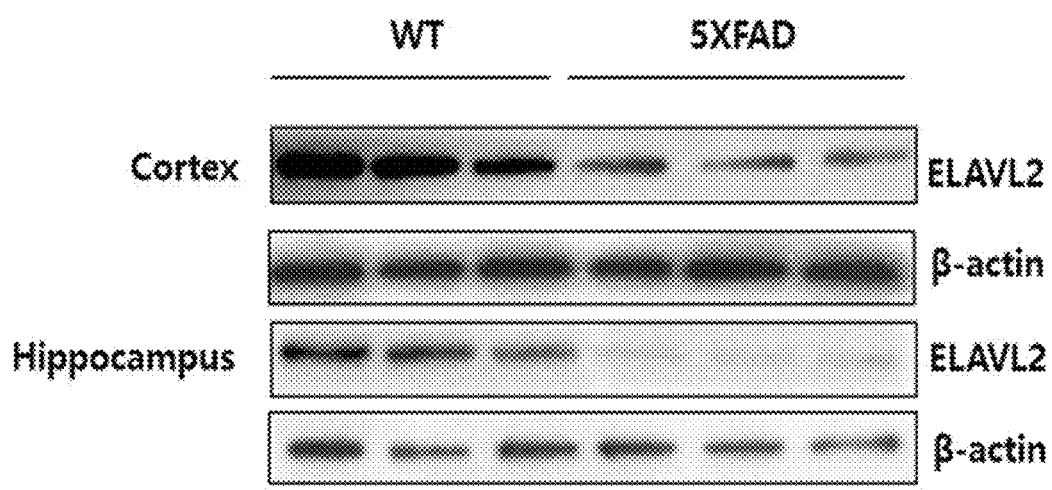
FIG. 6 shows a result of comparing the expression of ELAVL2 in the cerebral cortex and the hippocampus of 5×FAD.

FIG. 6 shows the expression of ELAVL2 in the cerebral cortex and hippocampus of 5×FAD. ELAVL2, an ELAV-like RNA-binding protein, is known as a protein that regulates neural functions such as neuronal excitation or synaptic transmission, which are directly associated with cognitive and behavioral functions. From FIG. 6, it was confirmed that the expression of ELAVL2 in the hippocampus and cerebral cortex of 5×FAD was decreased as compared to WT. This suggests that the dementia induced in 5×FAD is associated with the decline in cognitive and behavioral functions caused by decreased ELAVL2.

EXAMPLE 5: PREPARATION OF HIPPOCAMPAL PRIMARY CELL LINE AND IN-VITRO TRANSFECTION WITH ANTAGOMIR (AM)-485-3P (1) Research Methods Primary cells derived from the tissues of the hippocampus and the cerebral cortex excised from the embryo of 5×FAD were cultured. The methods for cell preparation and culture followed the previous research (Seibenhener, M. L & Woonten M. W, Isolation and culture of Hippocampal Neurons from Prenatal Mice, Jove, 2012). 50 nM of miR-485-3p duplex (or scrambled miRNA duplex; Bioneer, Daejon, South Korea) and 50 nM of antagomir (AM) 485-3p were transfected into primary cells in vitro using Lipofectamine 2000. A cell homogenate was obtained 48 hours after the transfection, which was subjected to western blot using ELAVL2 antibody (Abeam, UK). The immunoreactive protein was visualized with a chemiluminescence reagent (GE Healthcare, UK) and was measured and quantified using a chemiluminescence analyzer (Fusion SL). The amyloid beta 42 protein was measured by using the mouse/rat amyloid beta (1-42) ELISA kit (IBL) according to the manufacturer's instructions.

(2) Research Results

Figure 7A:
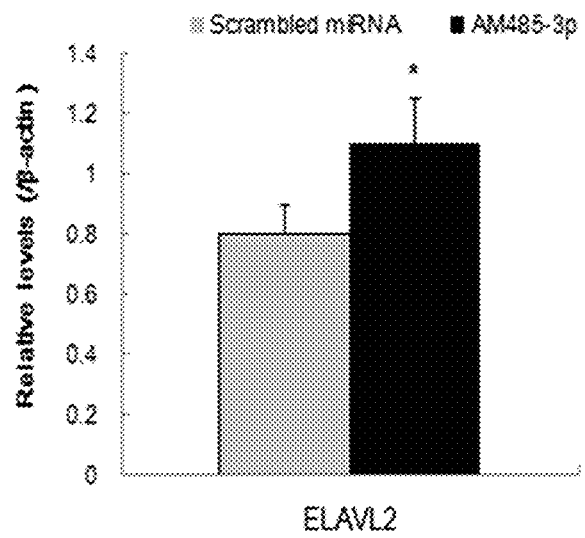
FIGS. 7A and 7B show results of comparing the expression of ELAVL2 (FIG. 7A) and Aβ (FIG. 7B) in hippocampal primary cells depending on transfection with antagomir (AM)-485-3p.
Figure 7B:
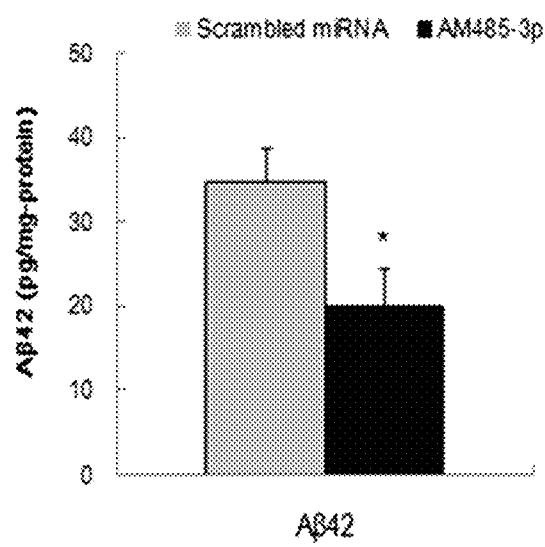

FIGS. 7A-7B show the results of comparing the expression of ELAVL2 and Aβ depending on transfection of hippocampal primary cells with AM-485-3p (2'-O-methylated-5'-GAGAGGAGAGCCGUGUAUGACU-3' (SEQ ID NO 9)).

It was confirmed that ELAVL2 was expressed in the hippocampal primary cells of 5×FAD, and the expression of ELAVL2 was increased in the cells transfected with antagomir (AM)-485-3p as compared to the control (FIG. 7 A). This means that miR-485-3p inhibits the expression of E1AVL2 in the cells treated with the antagomir. Because ELAVL2 is an important factor affecting cognitive function by being involved in excitation of neurons, the development of a drug or a composition that increases ELAVL2, such as a miR-485-3p inhibitor, can be a key strategy in preventing or treating Alzheimer's disease.

Also, it was confirmed that the expression of Aβ 42 was decreased in the cells transfected with AM-485-3p ((2'-O-methylated-5'-GAGAGGAGAGCCGUGUAUGACU-3' (SEQ ID NO 9); FIG. 7B). This means that miR-485-3p affects the production of Aβ 42 and suggests that the development of a drug or a composition capable of inhibiting miR-485-3p can relieve the pathological symptoms of Alzheimer's dementia by inhibiting the accumulation of Aβ.

EXAMPLE 6: IMAGING ANALYSIS OF DRUG DELIVERY AFTER INTRANASAL ADMINISTRATION OF CY3-AM-485-3P (1) Research Methods The inhibition of miR-485-3p was induced by intranasally administering a sequence-specific antagomir. The intranasal administration of the antagomir was carried out according to a method targeting the brain without anesthetizing the mouse (Leah R. T., et al. (2013) Intranasal Administration of CNS Therapeutics to Awake Mice. J Vis Exp. 2013; (74): 4440). After immobilizing the accustomed mouse for intranasal inhalation (intranasal grip) and positioning so that the abdomen faces upward, a pipette was positioned in front of one nasal cavity. 6 μL was inhaled dropwise twice using the pipette (1 drop=3 μL). After maintaining the position for 15 seconds, intranasal inhalation into the right nasal cavity was conducted in the same manner. The same procedure was repeated 2 minutes later. A total of 24 μL was inhaled (AM485 (2'-O-methylated)-5'-gagaggagagccguguaugacu-3' (SEQ ID NO 9); 5 nmol in 24 μL of distilled water treated with 0.1% v/v diethylpyrocarbonate; Bioneer, Korea). A vehicle of the same volume was administered to a control mouse. 12 weeks after the nasal administration, the anesthetized mouse was sacrificed by decapitation and the brain was excised immediately. After fixing the sagittally sectioned brain tissue, the tissue was treated with DAPI to stain DNA. The stained sample was imaged using a confocal laser scanning microscope (LSM510).

(2) Research Results

Figure 8A:
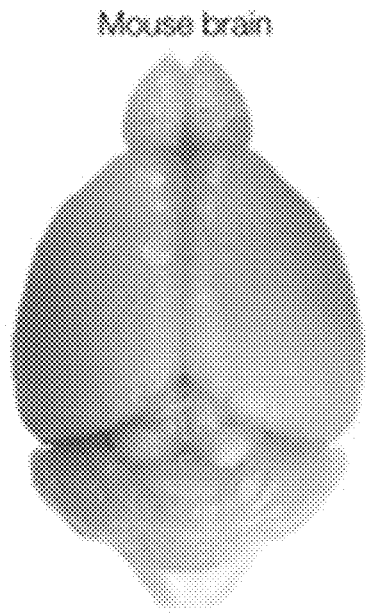
FIG. 8A-8B show an photograph of a mouse brain (FIG. 8A) and an imaging analysis of drug delivery after intranasal administration of Cy3-AM-485-3p (FIG. 8B).
Figure 8B:
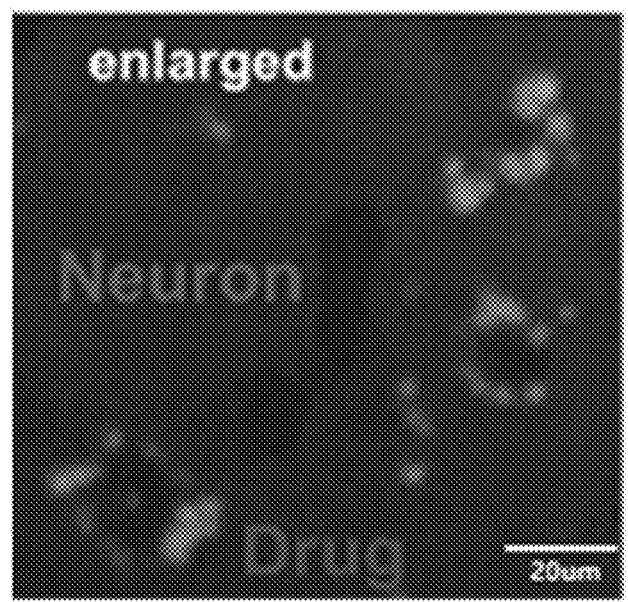

As a result of intranasally administering the AM-485-3p (2'-O-methylated-5'-GAGAGGAGAGCCGUGUAUGACU-3' (SEQ ID NO 9)) fluorescence-labeled with Cy3, it was confirmed that the target neurons were stained with DAPI (FIG. 8B).

EXAMPLE 7: COMPARATIVE QUANTITATIVE ANALYSIS OF ELAVL2 AND Aβ IN 5×FAD INTRANASALLY TREATED WITH ANTAGOMIR (AM)-485-3P (1) Research Methods The intranasal administration of AM-485-3p (2'-O-methylated-5'-GAGAGGAGAGCCGUGUAUGACU-3' (SEQ ID NO 9)) was conducted as described in Example 6 (Lee, S. T. et al. (2012) miR-206 regulates brain-derived neurotrophic factor in Alzheimer disease model. *Ann Neurol,* 72, 269-277). For intranasal administration of the antagomir, an anesthetized mouse was placed in supine position with its head flat on the surface. AM-485 (2'-O-methylated-5'-GAGAGGAGAGCCGUGUAUGACU-3' (SEQ ID NO 9); 5 nmol in 24 μL of distilled water treated with 0.1% v/v diethylpyrocarbonate; Bioneer, Korea) was administered with a pipette while alternating nares every 2 minutes, with 4 μL per each administration (6 times in total). A vehicle of the same volume was administered to a control mouse. On day 7 after the intranasal administration, the anesthetized mouse was sacrificed by decapitation and the brain was excised immediately. After preparing a homogenate of the brain (hippocampus and cerebral cortex), western blot was conducted using ELAVL2 antibody (Abcam, USA). The immunoreactive protein was visualized with a chemiluminescence reagent (GE Healthcare, UK) and was measured and quantified using a chemiluminescence analyzer (Fusion SL). Aβ 42 was measured by using the mouse/rat amyloid beta (1-42) ELISA kit (IBL) according to the manufacturer's instructions.

(2) Research Results

Figure 9A:
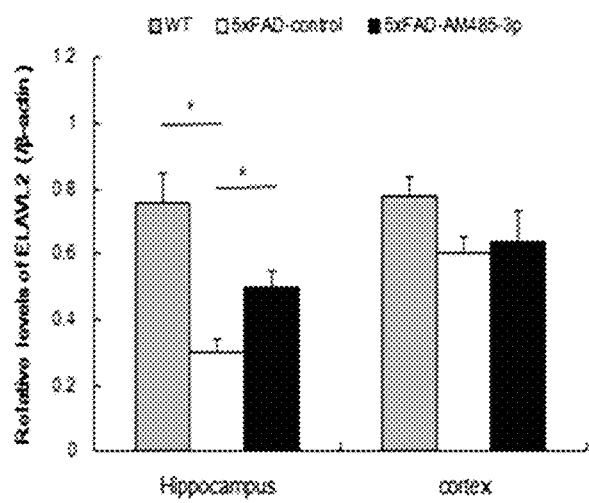
FIGS. 9A-9B show comparative quantitative analysis results of ELAVL2 (FIG. 9A) and Aβ (FIG. 9B) for 5×FAD intranasally treated with AM-485-3p.
Figure 9B:
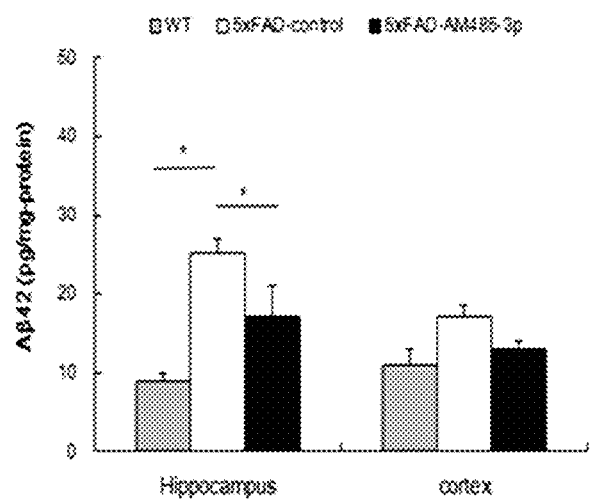

FIGS. 9A-9B show the comparative quantitative analysis of ELAVL2 and Aβ in 5×FAD intranasally treated with the AM-485-3p (2'-O-methylated-5'-GAGAGGAGAGCCGUGUAUGACU-3' (SEQ ID NO 9)). Because it was confirmed that the treatment of a mouse primary cell line with AM-485-3p induces change in ELAVL2 and Aβ (Example 5), the effect of AM-485-3p in vivo was investigated by intranasally treating 5×FAD with AM-485-3p. The AM-485-3p group showed increased expression of ELAVL2 as compared to the control group (FIG. 9 A). This suggests that the expression of ELAVL2 is decreased as the expression of miR-485-3p is increased, and that the decreased level of ELAVL2 can be increased by treating with a miR-485-3p inhibitor such as AM-485-3p.

In addition, since it was confirmed in the animal model that the treatment with AM-485-3p affects the inhibition of Aβ42 production (FIG. 9 B), it can be seen that treatment with the related inhibitor or drug can relieve the pathological symptoms of Alzheimer's dementia.

EXAMPLE 8: EXPRESSION PATTERN OF APP AND PATTERN OF TAU AND P-TAU IN HELA CELLS STABLY TRANSFECTED WITH SWEDISH MUTANT FORM OF AβPP (AβPPSW) DEPENDING ON TREATMENT WITH AM-485-3P (1) Research Methods HeLa cells in which AβPPsw was expressed stably were transfected with 5-500 or 50 nM of miR-485-3p duplex (or scrambled miRNA duplex; Bioneer, Daejon, South Korea) and 50 nM of antagomir (AM)-485-3p in vitro using Lipofectamine 2000. A cell homogenate was obtained 48 hours after the transfection, which was subjected to western blot using APP antibody (Cell Signaling, USA), Tau (Thermofisher Scientific) and p-Tau (Thermofisher Scientific). The immunoreactive protein was visualized with a chemiluminescence reagent (GE Healthcare, UK) and was measured and quantified using a chemiluminescence analyzer (Fusion SL).

(2) Research Results

Figure 10A:
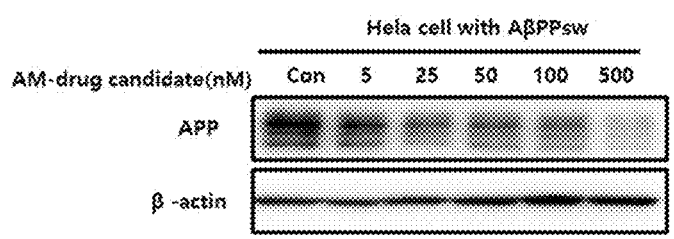
FIGS. 10A-10B show a results of comparing the expression of APP (FIGS. 10A-10B), tau (FIG. 10B), and p-tau (FIG. 10B) in HeLa cells depending on AM-485-3p transfection.
Figure 10B:
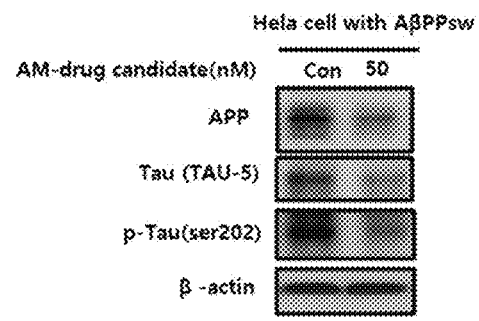

The expression of APP and pattern of Tau and p-Tau in the HeLa cells depending on the treatment with AM-485-3p (2'-O-methylated-5'-GAGAGGAGAGCCGUGUAUGACU-3' (SEQ ID NO 9)) was compared (FIGS. 10A-10B). It was confirmed that the expression of APP is decreased in the cells transfected with AM-485-3p in a concentration-dependent manner as compared to the control group. In addition, it was confirmed that the HeLa cell treated with 50 nM of AM-485-3p showed decreased phosphorylation of tau protein, which is known as another cause of Alzheimer's disease. This suggests that the development of a drug such as a miR-485-3p inhibitor or a composition thereof can be a key strategy in preventing or treating Alzheimer's disease by inhibiting the precursor of amyloid beta and the phosphorylation of tau protein, which are known as main causes of Alzheimer's disease, at the same time.

EXAMPLE 9: CONFIRMATION OF IMPROVED COGNITIVE FUNCTION IN 5×FAD MOUSE INTRANASALLY TREATED WITH ANTAGOMIR (AM)-485-3P (1) Research Methods Y-maze and passive avoidance tests were carried out to investigate whether the intranasal treatment of AM-485-3p (2'-O-methylated-5'-GAGAGGAGAGCCGUGUAUGACU-3' (SEQ ID NO 9)) improved the cognitive function of 5×FAD.

1) Y-Maze Test

A Y-maze test apparatus is composed of Y-shaped maze prepared with black acrylic plates (10 cm wide, 41 cm long, 25 cm high). The maze is arranged with an angle of 120°. After dividing each maze into A, B and C zones, the experimental animals were placed carefully in each zone and allowed to move freely for 8 minutes. Spontaneous alternation (%) was evaluated by measuring the number and sequence of entries into each maze. The entrance into the three different zones in sequence was given one point (actual alternation, e.g., A-B-C, B-C-A, C-A-B, etc.). No point was given to discontinuous entrance. The spontaneous alternation (%) was calculated by the following formula.

% Spontaneous alteration=total number of alternation/(total number of entries−2)×100

2) Passive Avoidance Test

The passive avoidance test is a widely used method for measuring the working memory ability of rodents. A passive avoidance test apparatus is a shuttle box divided into two chambers, one equipped with a light bulb to create a bright environment that the test animals dislike, and the other with light blocked to create an environment which is comfort for the animals. After two hours of stress application, the passive avoidance response was tested (training test). Aluminum grids were placed on the floor of the dark chamber at regular intervals so as to apply electric shocks to the sole of the animals. The experimental animals tend to enter the dark chamber. After keeping the animal in the bright chamber and then allowing to enter the dark chamber, electric shock (5 V, 0.5 mA, 10 sec) was applied so that it could remember it. 24 hours later, the time (latency time) lapsed until the entry into the dark chamber was measured up to 90 seconds without applying electric shock (retention tests 1, 2 and 3).

(2) Research Results

Figure 11A:
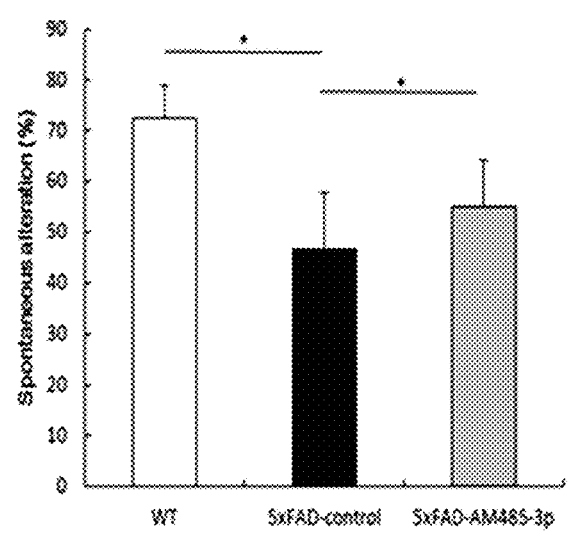
FIGS. 11A-11B show results of comparing the cognitive function of 5×FAD intranasally treated with AM-485-3p.
Figure 11B:
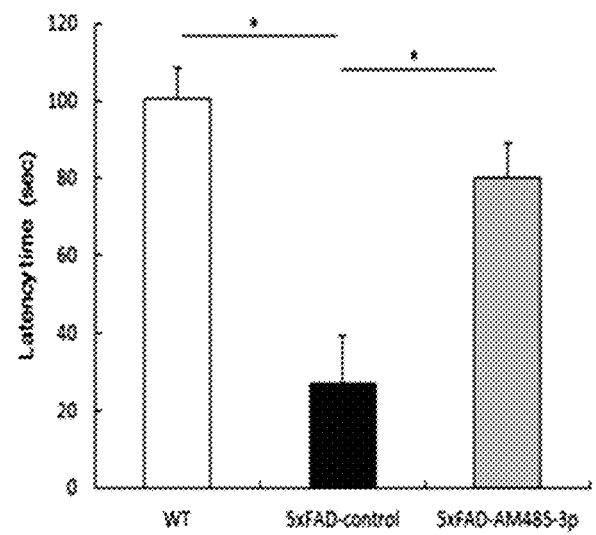

FIGS. 11A-11B show the results of comparing the cognitive function of the 5×FAD intranasally treated with AM-485-3p (2'-O-methylated-5'-GAGAGGAGAGCCGUGUAUGACU-3' (SEQ ID NO 9)). As a result, both the spontaneous alteration and the latency time were decreased in the 5×FAD and the control mouse as compared to WT. Because the typical symptoms of Alzheimer's dementia are behavior disorder and memory decline, the behavior disorder of 5×FAD seems to be due to the excessive accumulation and pathology of Aβ. However, the group intranasally treated with AM-485-3p showed significant increase in both the spontaneous alteration (FIG. 011 A) and the latency time (FIG. 11 B) as compared to 5×FAD. It means that the treatment with AM-485-3p can improve the main symptoms of Alzheimer's by relieving the pathological symptoms such as behavioral disorder and memory decline caused by the production of Aβ42 facilitated by miR-485-3p. Therefore, the preparation of a drug that regulates miR-485-3p or a composition thereof can be a new strategy to improve the main symptoms of Alzheimer's dementia, i.e., behavioral disorder and cognitive function.

EXAMPLE 10: STATISTICAL ANALYSIS

Two groups were compared by the Student's t-test, and three or more groups were compared by the Krushall-Wallis test. When the P value obtained from the Krushall-Wallis test was <0.05, two groups were tested post-hoc by the Mann-Whitney U test. P value of 0.05 or smaller for the two-tailed test was considered statistically significant.

INDUSTRIAL APPLICABILITY

According to the present disclosure, a composition for treating a brain disease, which contains a miR-485-3p inhibitor, can restore the ELAVL2 protein unlike the exiting therapeutic agents for Alzheimer's disease, which are limited only to alleviating symptoms by inducing decreased expression of amyloid beta 42. Therefore, it can fundamentally treat various diseases caused by decreased expression of ELAVL2, such as Alzheimer's disease, autism spectrum disorder, mental retardation, amyotrophic lateral sclerosis, etc. Accordingly, the present disclosure is useful for treating brain diseases including Alzheimer's disease fundamentally.

While the specific embodiments of the present disclosure have been described in detail above, those skilled of ordinary skill in the art will appreciate that the specific embodiments are merely specific exemplary embodiments and the scope of the present disclosure is not limited by them. It is to be understood that the substantial scope of the disclosure is defined by the appended claims and their equivalents.

The invention claimed is:

1. A method of treating a brain disease in a subject in need thereof comprising administering a miR-485-3p inhibitor to the subject, wherein the brain disease is selected from the group consisting of amyotrophic lateral sclerosis (ALS), autism spectrum disorder, mental retardation, seizure, stroke, Parkinson's disease, spinal cord injury, and combinations thereof, and wherein the miR-485-3p inhibitor comprises a nucleic acid molecule and inhibits expression of miR-485-3p.

2. The method of claim 1, wherein the miR-485-3p inhibitor is capable of inhibiting the interaction between miR-485-3p and the 3'-UTR of ELAV-like RNA binding protein 2 (ELAVL2).

3. The method of claim 1, wherein the miR-485-3p inhibitor is capable of binding to all or a part of a base sequence of the nucleic acid sequence set forth in SEQ ID NO 1 or SEQ ID NO 2.

4. The method of claim 1, wherein the nucleic acid molecule is selected from a group consisting of a DNA, an RNA, an antagomir, a siRNA, a shRNA, and an oligonucleotide.

5. The method of claim 1, wherein the nucleic acid molecule is an antisense oligonucleotide comprising a sequence partially or completely complementary to the base sequence of the nucleic acid sequence set forth in SEQ ID NO 1.

6. The method of claim 5, wherein the antisense oligonucleotide comprises the nucleic acid sequence set forth in SEQ ID NO: 3, SEQ ID NO: 4, SEQ ID NO: 5, SEQ ID NO: 6, or SEQ ID NO: 7.

7. The method of claim 5, wherein the antisense oligonucleotide comprises one or more modification selected from: 1) modification to a LNA (locked nucleic acid) or PNA (peptide nucleic acid) form; 2) substitution of the —OH group at the 2' carbon of a nucleotide with —CH$_3$ (methyl); and 3) modification of a nucleotide bond to phosphorothioate.

8. The method of claim 1, wherein the miR-485-3p inhibitor has one or more of the following features: 1) capable of increasing the expression level of ELAVL2; 2) capable of inhibiting the production of amyloid beta 42 (Aβ42); 3) capable of inhibiting the expression of amyloid precursor protein (APP); and 4) capable of inhibiting the phosphorylation of a tau protein.

9. The method of claim 1, wherein the miR-485-3p inhibitor is administered to the subject via intranasal administration, intravenous administration, subcutaneous injection, intrathecal injection, inhalation administration, or oral administration.

10. The method of claim 1, wherein the brain disease is associated with a decreased expression level of ELAVL2.

11. A method of treating a brain disease in a subject in need thereof comprising administering a miR-485-3p inhibitor to the subject, wherein the brain disease is associated with a decreased expression level of ELAV-like RNA binding protein 2 (ELAVL2), and wherein the miR-485-3p inhibitor comprises an antisense oligonucleotide that is capable of binding to the nucleic acid sequence set forth in SEQ ID NO: 1 or SEQ ID NO: 2.

12. The method of claim 11, wherein the antisense oligonucleotide comprises the nucleic acid sequence set forth in SEQ ID NO: 3, SEQ ID NO: 4, SEQ ID NO: 5, SEQ ID NO: 6, or SEQ ID NO: 7.

13. The method of claim 11, wherein the antisense oligonucleotide comprises one or more modification selected from: 1) modification to a LNA (locked nucleic acid) or PNA (peptide nucleic acid) form; 2) substitution of the —OH group at the 2' carbon of a nucleotide with —CH$_3$ (methyl); and 3) modification of a nucleotide bond to phosphorothioate.

14. The method of claim 11, wherein the antisense oligonucleotide comprises at least one base with a 2'-methoxy group, at least one base with a 3'-cholesterol, at least one phosphorothioate bond, or combinations thereof.

15. The method of claim 12, wherein the antisense oligonucleotide comprises the nucleic acid sequence set forth in SEQ ID NO: 7.

16. The method of claim 11, wherein the brain disease is selected from the group consisting of amyotrophic lateral sclerosis (ALS), autism spectrum disorder, mental retardation, seizure, stroke, Parkinson's disease, spinal cord injury, and combinations thereof.

17. The method of claim 13, wherein the antisense oligonucleotide is 2'-O-methylated.

18. The method of claim 7, wherein the antisense oligonucleotide is 2'-O-methylated.

19. The method of claim 6, wherein the antisense oligonucleotide comprises the nucleic acid sequence set forth in SEQ ID NO: 7.

* * * * *

SEQUENCE LISTING

<160> NUMBER OF SEQ ID NOS: 9

<210> SEQ ID NO 1
<211> LENGTH: 22
<212> TYPE: RNA
<213> ORGANISM: Artificial Sequence
<220> FEATURE:
<223> OTHER INFORMATION: miR-485-3p

<400> SEQUENCE: 1
gucauacacg gcucuccucu cu                                              22

<210> SEQ ID NO 2
<211> LENGTH: 73
<212> TYPE: RNA
<213> ORGANISM: Artificial Sequence
<220> FEATURE:
<223> OTHER INFORMATION: miR-485-3p

<400> SEQUENCE: 2
acuuggagag aggcuggccg ugaugaauuc gauucaucaa agcgagucau acacggcucu     60
ccucucuuuu agu                                                        73

<210> SEQ ID NO 3
<211> LENGTH: 9

```
<212> TYPE: RNA
<213> ORGANISM: Artificial Sequence
<220> FEATURE:
<223> OTHER INFORMATION: miR-485-3p

<400> SEQUENCE: 3 guguaugac                                                                  9

<210> SEQ ID NO 4
<211> LENGTH: 8
<212> TYPE: RNA
<213> ORGANISM: Artificial Sequence
<220> FEATURE:
<223> OTHER INFORMATION: miR-485-3p

<400> SEQUENCE: 4 uguaugac                                                                   8

<210> SEQ ID NO 5
<211> LENGTH: 8
<212> TYPE: RNA
<213> ORGANISM: Artificial Sequence
<220> FEATURE:
<223> OTHER INFORMATION: miR-485-3p

<400> SEQUENCE: 5 guguauga                                                                   8

<210> SEQ ID NO 6
<211> LENGTH: 7
<212> TYPE: RNA
<213> ORGANISM: Artificial Sequence
<220> FEATURE:
<223> OTHER INFORMATION: miR-485-3p

<400> SEQUENCE: 6 uguauga                                                                    7

<210> SEQ ID NO 7
<211> LENGTH: 22
<212> TYPE: RNA
<213> ORGANISM: Artificial Sequence
<220> FEATURE:
<223> OTHER INFORMATION: miR-485-3p

<400> SEQUENCE: 7
agagaggaga gccguguaug ac                                                  22

<210> SEQ ID NO 8
<211> LENGTH: 22
<212> TYPE: RNA
<213> ORGANISM: Artificial Sequence
<220> FEATURE:
<223> OTHER INFORMATION: mmu-miR-485-3p

<400> SEQUENCE: 8
agucauacac ggcucuccuc uc                                                  22

<210> SEQ ID NO 9
<211> LENGTH: 22
<212> TYPE: RNA
```

```
<213> ORGANISM: Artificial Sequence
<220> FEATURE:
<223> OTHER INFORMATION: antagomir

<400> SEQUENCE: 9
gagaggagag ccguguauga cu                                              22
```